US009309287B2

(12) United States Patent
Toshchakov

(10) Patent No.: US 9,309,287 B2
(45) Date of Patent: Apr. 12, 2016

(54) INHIBITORS OF TLR SIGNALING BY TARGETING TIR DOMAIN INTERFACES

(71) Applicant: UNIVERSITY OF MARYLAND, BALTIMORE, Baltimore, MD (US)

(72) Inventor: Vladimir Toshchakov, Owings Mills, MD (US)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 0 days.

(21) Appl. No.: 14/581,752

(22) Filed: Dec. 23, 2014

(65) Prior Publication Data

US 2016/0039901 A1     Feb. 11, 2016

Related U.S. Application Data

(62) Division of application No. 13/761,277, filed on Feb. 7, 2013, now Pat. No. 8,940,703.

(60) Provisional application No. 61/595,727, filed on Feb. 7, 2012.

(51) Int. Cl.
| | |
|---|---|
| *C07K 7/08* | (2006.01) |
| *A61K 38/10* | (2006.01) |
| *C07K 14/705* | (2006.01) |
| *C07K 7/06* | (2006.01) |

(52) U.S. Cl.
CPC ... *C07K 7/08* (2013.01); *C07K 7/06* (2013.01); *C07K 14/705* (2013.01)

(58) Field of Classification Search
CPC .......... C07K 14/705; C07K 7/06; C07K 7/08; C07K 2319/00; C07K 14/005; A61K 38/00; A61K 47/48246; G01N 2500/10
See application file for complete search history.

(56) References Cited

FOREIGN PATENT DOCUMENTS

WO     2006/113530     10/2006

OTHER PUBLICATIONS

Toshchakov, V.Y., et al., Targeting TLR4 Signaling by TLR4 Toll/IL-1 Receptor Domain-Derived Decoy Peptides: Identification of the TLR4 Toll/IL-1 Receptor Domain Dimerization Interface, The Journal of Immunology, 186(8):4819-4827 (Mar. 14, 2011).

Couture, L. et al., Targeting Toll-Like Receptor (TLR) Signaling by Toll/Interleukin-1 Receptor (TIR) Domain-containing Adapter Protein/MyD88 Adapter-like (TIRAP/MAL)-derived Decoy Peptides; The Journal of Biological Chemistry, vol. 287(29):24641-24648 (May 30, 2012).

*Primary Examiner* — James H Alstrum Acevedo
*Assistant Examiner* — Randall L Beane
(74) *Attorney, Agent, or Firm* — Wenderoth, Lind & Ponack, L.L.P.

(57) ABSTRACT

TIR-domain decoy peptides and TIR domain peptides are disclosed, as well as methods of using the peptides in the regulation of toll-like receptor (TLR) activation and signaling.

2 Claims, 18 Drawing Sheets

SEQUENCE LISTING

<160> NUMBER OF SEQ ID NOS: 84

<210> SEQ ID NO 1
<211> LENGTH: 26
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 1

Arg Gln Ile Lys Ile Trp Phe Gln Asn Arg Arg Met Lys Trp Lys Lys
1               5                   10                  15

Glu Gly Ser Gln Ala Ser Leu Arg Cys Phe
            20                  25

```
<210> SEQ ID NO 2
<211> LENGTH: 28
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 2

Arg Gln Ile Lys Ile Trp Phe Gln Asn Arg Arg Met Lys Trp Lys Lys
1               5                   10                  15

Glu Leu Cys Gln Ala Leu Ser Arg Ser His Cys Arg
            20                  25

<210> SEQ ID NO 3
<211> LENGTH: 30
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 3

Arg Gln Ile Lys Ile Trp Phe Gln Asn Arg Arg Met Lys Trp Lys Lys
1               5                   10                  15

Pro Gly Phe Leu Arg Asp Pro Trp Cys Lys Tyr Gln Met Leu
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 4

Arg Gln Ile Lys Ile Trp Phe Gln Asn Arg Arg Met Lys Trp Lys Lys
1               5                   10                  15

Ala Ala Tyr Pro Pro Glu Leu Arg Phe Met Tyr Tyr Val Asp
            20                  25                  30

<210> SEQ ID NO 5
<211> LENGTH: 29
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 5

Arg Gln Ile Lys Ile Trp Phe Gln Asn Arg Arg Met Lys Trp Lys Lys
1               5                   10                  15

Gly Gly Phe Tyr Gln Val Lys Glu Ala Val Ile His Tyr
            20                  25

<210> SEQ ID NO 6
<211> LENGTH: 30
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 6

Arg Gln Ile Lys Ile Trp Phe Gln Asn Arg Arg Met Lys Trp Lys Lys
```

```
1               5                   10                  15
Ile Val Phe Ala Glu Met Pro Cys Gly Arg Leu His Leu Gln
                20                  25                  30

<210> SEQ ID NO 7
<211> LENGTH: 25
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 7

Arg Gln Ile Lys Ile Trp Phe Gln Asn Arg Arg Met Lys Trp Lys Lys
1               5                   10                  15
Ile Val Phe Ala Glu Met Pro Cys Gly
                20                  25

<210> SEQ ID NO 8
<211> LENGTH: 30
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 8

Arg Gln Ile Lys Ile Trp Phe Gln Asn Arg Arg Met Lys Trp Lys Lys
1               5                   10                  15
Glu Asn Phe Leu Arg Asp Thr Trp Cys Asn Phe Gln Phe Tyr
                20                  25                  30

<210> SEQ ID NO 9
<211> LENGTH: 29
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 9

Arg Gln Ile Lys Ile Trp Phe Gln Asn Arg Arg Met Lys Trp Lys Lys
1               5                   10                  15
Cys Glu Glu Phe Gln Val Pro Gly Arg Gly Glu Leu His
                20                  25

<210> SEQ ID NO 10
<211> LENGTH: 28
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 10

Arg Gln Ile Lys Ile Trp Phe Gln Asn Arg Arg Met Lys Trp Lys Lys
1               5                   10                  15
Cys Leu Gln Asp Ala Ile Asp His Ser Gly Phe Thr
                20                  25

<210> SEQ ID NO 11
<211> LENGTH: 25
<212> TYPE: PRT
<213> ORGANISM: Artificial Sequence
<220> FEATURE:
```

<223> OTHER INFORMATION: Antennapedia homeodomain translocating
    segment-TIR domain fusion

<400> SEQUENCE: 11

Arg Gln Ile Lys Ile Trp Phe Gln Asn Arg Arg Met Lys Trp Lys Lys
1               5                   10                  15

Cys Leu Gln Asp Ala Ile Asp His Ser
            20                  25

<210> SEQ ID NO 12
<211> LENGTH: 26
<212> TYPE: PRT
<213> ORGANISM: Artificial Sequence
<220> FEATURE:
<223> OTHER INFORMATION: Antennapedia homeodomain translocating
    segment-TIR domain fusion

<400> SEQUENCE: 12

Arg Gln Ile Lys Ile Trp Phe Gln Asn Arg Arg Met Lys Trp Lys Lys
1               5                   10                  15

Glu Gln Thr Asp Tyr Arg Leu Lys Leu Cys
            20                  25

<210> SEQ ID NO 13
<211> LENGTH: 29
<212> TYPE: PRT
<213> ORGANISM: Artificial Sequence
<220> FEATURE:
<223> OTHER INFORMATION: Antennapedia homeodomain translocating
    segment-TIR domain fusion

<400> SEQUENCE: 13

Arg Gln Ile Lys Ile Trp Phe Gln Asn Arg Arg Met Lys Trp Lys Lys
1               5                   10                  15

Ser Asp Arg Asp Val Leu Pro Gly Thr Cys Val Trp Ser
            20                  25

<210> SEQ ID NO 14
<211> LENGTH: 29
<212> TYPE: PRT
<213> ORGANISM: Artificial Sequence
<220> FEATURE:
<223> OTHER INFORMATION: Antennapedia homeodomain translocating
    segment-TIR domain fusion

<400> SEQUENCE: 14

Arg Gln Ile Lys Ile Trp Phe Gln Asn Arg Arg Met Lys Trp Lys Lys
1               5                   10                  15

Ile Ala Ser Glu Leu Ile Glu Lys Arg Cys Arg Arg Met
            20                  25

<210> SEQ ID NO 15
<211> LENGTH: 30
<212> TYPE: PRT
<213> ORGANISM: Artificial Sequence
<220> FEATURE:
<223> OTHER INFORMATION: Antennapedia homeodomain translocating
    segment-TIR domain fusion

<400> SEQUENCE: 15

Arg Gln Ile Lys Ile Trp Phe Gln Asn Arg Arg Met Lys Trp Lys Lys
1               5                   10                  15

Ala Gly Cys Lys Lys Tyr Ser Arg Gly Glu Ser Ile Tyr Asp
            20                  25                  30

<210> SEQ ID NO 16
<211> LENGTH: 26
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 16

Arg Gln Ile Lys Ile Trp Phe Gln Asn Arg Arg Met Lys Trp Lys Lys
1               5                   10                  15

Glu Glu Gly Val Pro Arg Phe His Leu Cys
            20                  25

<210> SEQ ID NO 17
<211> LENGTH: 30
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 17

Arg Gln Ile Lys Ile Trp Phe Gln Asn Arg Arg Met Lys Trp Lys Lys
1               5                   10                  15

Leu His Tyr Arg Asp Phe Ile Pro Gly Val Ala Ile Ala Ala
            20                  25                  30

<210> SEQ ID NO 18
<211> LENGTH: 29
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 18

Arg Gln Ile Lys Ile Trp Phe Gln Asn Arg Arg Met Lys Trp Lys Lys
1               5                   10                  15

Leu Arg Gln Gln Val Glu Leu Tyr Arg Leu Leu Ser Arg
            20                  25

<210> SEQ ID NO 19
<211> LENGTH: 29
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 19

Arg Gln Ile Lys Ile Trp Phe Gln Asn Arg Arg Met Lys Trp Lys Lys
1               5                   10                  15

His Ile Phe Trp Arg Arg Leu Lys Asn Ala Leu Leu Asp
            20                  25

<210> SEQ ID NO 20
<211> LENGTH: 30
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 20

-continued

```
Arg Gln Ile Lys Ile Trp Phe Gln Asn Arg Met Lys Trp Lys Lys
1               5                  10                  15
Arg Lys Pro Lys Lys Ala Pro Cys Arg Asp Val Cys Tyr Asp
            20                  25                  30

<210> SEQ ID NO 21
<211> LENGTH: 26
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 21

Arg Gln Ile Lys Ile Trp Phe Gln Asn Arg Met Lys Trp Lys Lys
1               5                  10                  15
Glu Asn Ser Asp Pro Pro Phe Lys Leu Cys
            20                  25

<210> SEQ ID NO 22
<211> LENGTH: 29
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 22

Arg Gln Ile Lys Ile Trp Phe Gln Asn Arg Met Lys Trp Lys Lys
1               5                  10                  15
Pro Gln Arg Phe Cys Lys Leu Arg Lys Ile Met Asn Thr
            20                  25

<210> SEQ ID NO 23
<211> LENGTH: 30
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 23

Arg Gln Ile Lys Ile Trp Phe Gln Asn Arg Met Lys Trp Lys Lys
1               5                  10                  15
Leu His Lys Arg Asp Phe Val Pro Gly Lys Trp Ile Ile Asp
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Antennapedia homeodomain translocating
      segment-TIR domain fusion

<400> SEQUENCE: 24

Arg Gln Ile Lys Ile Trp Phe Gln Asn Arg Met Lys Trp Lys Lys
1               5                  10                  15
Glu Pro Ile Glu Arg Lys Ala Ile Pro Gln Arg Phe Cys Lys
            20                  25                  30

<210> SEQ ID NO 25
<211> LENGTH: 10
<212> TYPE: PRT
<213> ORGANISM: Mus musculus
```

<400> SEQUENCE: 25

Glu Gly Ser Gln Ala Ser Leu Arg Cys Phe
1               5                   10

<210> SEQ ID NO 26
<211> LENGTH: 12
<212> TYPE: PRT
<213> ORGANISM: Mus musculus

<400> SEQUENCE: 26

Glu Leu Cys Gln Ala Leu Ser Arg Ser His Cys Arg
1               5                   10

<210> SEQ ID NO 27
<211> LENGTH: 14
<212> TYPE: PRT
<213> ORGANISM: Mus musculus

<400> SEQUENCE: 27

Pro Gly Phe Leu Arg Asp Pro Trp Cys Lys Tyr Gln Met Leu
1               5                   10

<210> SEQ ID NO 28
<211> LENGTH: 14
<212> TYPE: PRT
<213> ORGANISM: Mus musculus

<400> SEQUENCE: 28

Ala Ala Tyr Pro Pro Glu Leu Arg Phe Met Tyr Tyr Val Asp
1               5                   10

<210> SEQ ID NO 29
<211> LENGTH: 13
<212> TYPE: PRT
<213> ORGANISM: Mus musculus

<400> SEQUENCE: 29

Gly Gly Phe Tyr Gln Val Lys Glu Ala Val Ile His Tyr
1               5                   10

<210> SEQ ID NO 30
<211> LENGTH: 14
<212> TYPE: PRT
<213> ORGANISM: Mus musculus

<400> SEQUENCE: 30

Ile Val Phe Ala Glu Met Pro Cys Gly Arg Leu His Leu Gln
1               5                   10

<210> SEQ ID NO 31
<211> LENGTH: 9
<212> TYPE: PRT
<213> ORGANISM: Mus musculus

<400> SEQUENCE: 31

Ile Val Phe Ala Glu Met Pro Cys Gly
1               5

<210> SEQ ID NO 32
<211> LENGTH: 14
<212> TYPE: PRT
<213> ORGANISM: Mus musculus

<400> SEQUENCE: 32

Glu Asn Phe Leu Arg Asp Thr Trp Cys Asn Phe Gln Phe Tyr
1               5                   10

<210> SEQ ID NO 33
<211> LENGTH: 13
<212> TYPE: PRT
<213> ORGANISM: Mus musculus

<400> SEQUENCE: 33

Cys Glu Glu Phe Gln Val Pro Gly Arg Gly Glu Leu His
1               5                   10

<210> SEQ ID NO 34
<211> LENGTH: 12
<212> TYPE: PRT
<213> ORGANISM: Mus musculus

<400> SEQUENCE: 34

Cys Leu Gln Asp Ala Ile Asp His Ser Gly Phe Thr
1               5                   10

<210> SEQ ID NO 35
<211> LENGTH: 9
<212> TYPE: PRT
<213> ORGANISM: Mus musculus

<400> SEQUENCE: 35

Cys Leu Gln Asp Ala Ile Asp His Ser
1               5

<210> SEQ ID NO 36
<211> LENGTH: 10
<212> TYPE: PRT
<213> ORGANISM: Mus musculus

<400> SEQUENCE: 36

Glu Gln Thr Asp Tyr Arg Leu Lys Leu Cys
1               5                   10

<210> SEQ ID NO 37
<211> LENGTH: 13
<212> TYPE: PRT
<213> ORGANISM: Mus musculus

<400> SEQUENCE: 37

Ser Asp Arg Asp Val Leu Pro Gly Thr Cys Val Trp Ser
1               5                   10

<210> SEQ ID NO 38
<211> LENGTH: 13
<212> TYPE: PRT
<213> ORGANISM: Mus musculus

<400> SEQUENCE: 38

Ile Ala Ser Glu Leu Ile Glu Lys Arg Cys Arg Arg Met
1               5                   10

<210> SEQ ID NO 39
<211> LENGTH: 14
<212> TYPE: PRT
<213> ORGANISM: Mus musculus

<400> SEQUENCE: 39

Ala Gly Cys Lys Lys Tyr Ser Arg Gly Glu Ser Ile Tyr Asp

```
1               5                   10

<210> SEQ ID NO 40
<211> LENGTH: 10
<212> TYPE: PRT
<213> ORGANISM: Mus musculus

<400> SEQUENCE: 40

Glu Glu Gly Val Pro Arg Phe His Leu Cys
1               5                   10

<210> SEQ ID NO 41
<211> LENGTH: 14
<212> TYPE: PRT
<213> ORGANISM: Mus musculus

<400> SEQUENCE: 41

Leu His Tyr Arg Asp Phe Ile Pro Gly Val Ala Ile Ala Ala
1               5                   10

<210> SEQ ID NO 42
<211> LENGTH: 13
<212> TYPE: PRT
<213> ORGANISM: Mus musculus

<400> SEQUENCE: 42

Leu Arg Gln Gln Val Glu Leu Tyr Arg Leu Leu Ser Arg
1               5                   10

<210> SEQ ID NO 43
<211> LENGTH: 13
<212> TYPE: PRT
<213> ORGANISM: Mus musculus

<400> SEQUENCE: 43

His Ile Phe Trp Arg Leu Lys Asn Ala Leu Leu Asp
1               5                   10

<210> SEQ ID NO 44
<211> LENGTH: 14
<212> TYPE: PRT
<213> ORGANISM: Mus musculus

<400> SEQUENCE: 44

Arg Lys Pro Lys Lys Ala Pro Cys Arg Asp Val Cys Tyr Asp
1               5                   10

<210> SEQ ID NO 45
<211> LENGTH: 10
<212> TYPE: PRT
<213> ORGANISM: Mus musculus

<400> SEQUENCE: 45

Glu Asn Ser Asp Pro Pro Phe Lys Leu Cys
1               5                   10

<210> SEQ ID NO 46
<211> LENGTH: 13
<212> TYPE: PRT
<213> ORGANISM: Mus musculus

<400> SEQUENCE: 46

Pro Gln Arg Phe Cys Lys Leu Arg Lys Ile Met Asn Thr
1               5                   10
```

<210> SEQ ID NO 47
<211> LENGTH: 14
<212> TYPE: PRT
<213> ORGANISM: Mus musculus

<400> SEQUENCE: 47

Leu His Lys Arg Asp Phe Val Pro Gly Lys Trp Ile Ile Asp
1               5                   10

<210> SEQ ID NO 48
<211> LENGTH: 14
<212> TYPE: PRT
<213> ORGANISM: Mus musculus

<400> SEQUENCE: 48

Glu Pro Ile Glu Arg Lys Ala Ile Pro Gln Arg Phe Cys Lys
1               5                   10

<210> SEQ ID NO 49
<211> LENGTH: 30
<212> TYPE: PRT
<213> ORGANISM: Artificial Sequence
<220> FEATURE:
<223> OTHER INFORMATION: Control peptide comprising random arrangement
      of amino acids

<400> SEQUENCE: 49

Arg Gln Ile Lys Ile Trp Phe Gln Asn Arg Arg Met Lys Trp Lys Lys
1               5                   10                  15

Ser Leu His Gly Arg Gly Asp Pro Met Glu Ala Phe Ile Ile
            20                  25                  30

<210> SEQ ID NO 50
<211> LENGTH: 16
<212> TYPE: PRT
<213> ORGANISM: Drosophilia melanogaster

<400> SEQUENCE: 50

Arg Gln Ile Lys Ile Trp Phe Gln Asn Arg Arg Met Lys Trp Lys Lys
1               5                   10                  15

<210> SEQ ID NO 51
<211> LENGTH: 22
<212> TYPE: DNA
<213> ORGANISM: Artificial Sequence
<220> FEATURE:
<223> OTHER INFORMATION: Chemically synthesized primer sequence

<400> SEQUENCE: 51
gctgacctgc tgattacatt aa                                                  22

<210> SEQ ID NO 52
<211> LENGTH: 28
<212> TYPE: DNA
<213> ORGANISM: Artificial Sequence
<220> FEATURE:
<223> OTHER INFORMATION: Chemically synthesized primer sequence

<400> SEQUENCE: 52
tgatcattac agtagctctt cagtctga                                            28

<210> SEQ ID NO 53
<211> LENGTH: 25
<212> TYPE: DNA
<213> ORGANISM: Artificial Sequence
<220> FEATURE:
<223> OTHER INFORMATION: Chemically synthesized primer sequence

<400> SEQUENCE: 53
gaccctcaca ctcagatcat cttct                                                25

<210> SEQ ID NO 54
<211> LENGTH: 21
<212> TYPE: DNA
<213> ORGANISM: Artificial Sequence
<220> FEATURE:
<223> OTHER INFORMATION: Chemically synthesized primer sequence

<400> SEQUENCE: 54
ccacttggtg gtttgctacg a                                                    21

<210> SEQ ID NO 55
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 55
aaatacctgt ggccttgggc                                                      20

<210> SEQ ID NO 56
<211> LENGTH: 21
<212> TYPE: DNA
<213> ORGANISM: Artificial Sequence
<220> FEATURE:
<223> OTHER INFORMATION: Chemically synthesized primer sequence

<400> SEQUENCE: 56
cttgggatcc acactctcca g                                                    21

<210> SEQ ID NO 57
<211> LENGTH: 25
<212> TYPE: DNA
<213> ORGANISM: Artificial Sequence
<220> FEATURE:
<223> OTHER INFORMATION: Chemically synthesized primer sequence

<400> SEQUENCE: 57
cacttgaaga gctattactg gaggg                                                25

<210> SEQ ID NO 58
<211> LENGTH: 18
<212> TYPE: DNA
<213> ORGANISM: Artificial Sequence
<220> FEATURE:
<223> OTHER INFORMATION: Chemically synthesized primer sequence

<400> SEQUENCE: 58
ctcggaccac catccagg                                                        18

<210> SEQ ID NO 59
<211> LENGTH: 21
<212> TYPE: DNA
<213> ORGANISM: Artificial Sequence
<220> FEATURE:
<223> OTHER INFORMATION: Chemically synthesized primer sequence

<400> SEQUENCE: 59
ctgctttgcc tacctctccc t                                                    21

```
<210> SEQ ID NO 60
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 60
gagtgacaaa cacgactgca agat                                              24

<210> SEQ ID NO 61
<211> LENGTH: 13
<212> TYPE: PRT
<213> ORGANISM: Mus musculus

<400> SEQUENCE: 61

Gln Leu Arg Asp Ala Ala Pro Gly Gly Ala Ile Val Ser
1               5                   10

<210> SEQ ID NO 62
<211> LENGTH: 14
<212> TYPE: PRT
<213> ORGANISM: Mus musculus

<400> SEQUENCE: 62

Arg His Phe Ile Gln Ser Arg Trp Cys Ile Phe Glu Tyr Glu
1               5                   10

<210> SEQ ID NO 63
<211> LENGTH: 14
<212> TYPE: PRT
<213> ORGANISM: Mus musculus

<400> SEQUENCE: 63

Gly Ala Gly Ala Glu Glu Gln Asp Glu Glu Phe Leu Lys
1               5                   10

<210> SEQ ID NO 64
<211> LENGTH: 14
<212> TYPE: PRT
<213> ORGANISM: Mus musculus

<400> SEQUENCE: 64

Ala Glu Asp Asp Thr Asp Glu Ala Leu Arg Val Gln Asp Leu
1               5                   10

<210> SEQ ID NO 65
<211> LENGTH: 9
<212> TYPE: PRT
<213> ORGANISM: Mus musculus

<400> SEQUENCE: 65

Gln Asn Asp Phe Gly Ile Arg Pro Gly
1               5

<210> SEQ ID NO 66
<211> LENGTH: 5
<212> TYPE: PRT
<213> ORGANISM: Mus musculus

<400> SEQUENCE: 66

Ile Val Phe Ala Glu
1               5
```

```
<210> SEQ ID NO 67
<211> LENGTH: 5
<212> TYPE: PRT
<213> ORGANISM: Mus musculus

<400> SEQUENCE: 67

Glu Met Pro Cys Gly
1               5

<210> SEQ ID NO 68
<211> LENGTH: 5
<212> TYPE: PRT
<213> ORGANISM: Mus musculus

<400> SEQUENCE: 68

Arg Leu His Leu Gln
1               5

<210> SEQ ID NO 69
<211> LENGTH: 9
<212> TYPE: PRT
<213> ORGANISM: Mus musculus

<400> SEQUENCE: 69

Ile Val Phe Ala Arg Leu His Leu Gln
1               5

<210> SEQ ID NO 70
<211> LENGTH: 9
<212> TYPE: PRT
<213> ORGANISM: Mus musculus

<400> SEQUENCE: 70

Ile Val Phe Ala Glu Met Pro Cys Gly
1               5

<210> SEQ ID NO 71
<211> LENGTH: 14
<212> TYPE: PRT
<213> ORGANISM: Mus musculus

<400> SEQUENCE: 71

Ile Val Phe Ala Ala Met Pro Cys Gly Arg Leu His Leu Gln
1               5                   10

<210> SEQ ID NO 72
<211> LENGTH: 14
<212> TYPE: PRT
<213> ORGANISM: Mus musculus

<400> SEQUENCE: 72

Ile Val Phe Ala Glu Met His Cys Gly Arg Leu His Leu Gln
1               5                   10

<210> SEQ ID NO 73
<211> LENGTH: 14
<212> TYPE: PRT
<213> ORGANISM: Mus musculus

<400> SEQUENCE: 73

Ile Val Phe Ala Glu Met Pro His Gly Arg Leu His Leu Gln
1               5                   10

<210> SEQ ID NO 74
<211> LENGTH: 12
```

```
<212> TYPE: PRT
<213> ORGANISM: Mus musculus

<400> SEQUENCE: 74

Asn Leu Asp Asp Ala Val Asn Gly Ser Ala Trp Thr
1               5                   10

<210> SEQ ID NO 75
<211> LENGTH: 15
<212> TYPE: PRT
<213> ORGANISM: Mus musculus

<400> SEQUENCE: 75

Thr Ser Leu Met Asn Ser Val Ser Arg Gln His Lys Tyr Asn Ser
1               5                   10                  15

<210> SEQ ID NO 76
<211> LENGTH: 10
<212> TYPE: PRT
<213> ORGANISM: Mus musculus

<400> SEQUENCE: 76

Arg Pro Leu Asn Ser Pro Leu Pro Arg Glu
1               5                   10

<210> SEQ ID NO 77
<211> LENGTH: 14
<212> TYPE: PRT
<213> ORGANISM: Mus musculus

<400> SEQUENCE: 77

Pro Arg Glu Arg Thr Pro Leu Ala Leu Gln Thr Ile Asn Ala
1               5                   10

<210> SEQ ID NO 78
<211> LENGTH: 11
<212> TYPE: PRT
<213> ORGANISM: Mus musculus

<400> SEQUENCE: 78

Arg Thr Pro Leu Ala Leu Gln Thr Ile Asn Ala
1               5                   10

<210> SEQ ID NO 79
<211> LENGTH: 10
<212> TYPE: PRT
<213> ORGANISM: Mus musculus

<400> SEQUENCE: 79

Gln Thr Ile Asn Ala Leu Glu Glu Glu Ser
1               5                   10

<210> SEQ ID NO 80
<211> LENGTH: 13
<212> TYPE: PRT
<213> ORGANISM: Mus musculus

<400> SEQUENCE: 80

Leu Glu Glu Glu Ser Gln Gly Phe Ser Thr Gln Val Glu
1               5                   10

<210> SEQ ID NO 81
<211> LENGTH: 13
<212> TYPE: PRT
<213> ORGANISM: Mus musculus
```

```
<400> SEQUENCE: 81

Arg Ile Phe Arg Glu Ser Val Phe Glu Arg Gln Gln Ser
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Control peptide comprising random arrangement
      of amino acids

<400> SEQUENCE: 82

Ser Leu His Gly Arg Gly Asp Pro Met Glu Ala Phe Ile Ile
1               5                   10

<210> SEQ ID NO 83
<211> LENGTH: 14
<212> TYPE: PRT
<213> ORGANISM: Mus musculus

<400> SEQUENCE: 83

Asp Asp Tyr Leu Gln Ser Lys Glu Cys Asp Phe Gln Thr Lys
1               5                   10

<210> SEQ ID NO 84
<211> LENGTH: 14
<212> TYPE: PRT
<213> ORGANISM: Mus musculus

<400> SEQUENCE: 84

Ala Ser Phe Asp Cys Ser Leu Ser Leu His Gln Ile Asn His
1               5                   10
```

INHIBITORS OF TLR SIGNALING BY TARGETING TIR DOMAIN INTERFACES

STATEMENT OF FEDERALLY SPONSORED RESEARCH AND DEVELOPMENT

This invention was made with government support under Grant Numbers AI082299 and AI018797 awarded by the National Institutes of Health. The government has certain rights in the invention.

TECHNICAL FIELD

The present invention relates to peptides and methods of using the peptides in the modification of inflammatory signaling and host defense pathways.

BACKGROUND OF INVENTION

Toll-like receptors (TLRs) are a large family of type I transmembrane proteins that function as "pattern recognition receptors." These receptors constitute an integral component of the innate immune system as they are able to recognize microbial products and pathogen-associated molecular patterns (PAMPs), as well as endogenous ligands associated with inflammation or danger-associated molecular patterns (DAMPs). TLRs thus sense a variety of conserved molecules. There are at least 13 recognized TLRs, termed TLR1, TLR2, TLR3, etc. Upon ligand binding, the receptors generally homodimerize, although TLR2 forms heterodimers with TLR1 or TLR6, with each dimer having a different ligand specificity. Activated TLRs initiate the innate immune response that enables the host to combat infection.

Each of the germline-encoded human TLRs is structurally similar, consisting of a leucine-rich repeat-containing extracellular domain, a membrane spanning helix and a cytosolic TIR (Toll/IL-1 Receptor) domain (2, 3). The TIR domain is a highly conserved structure which is found in both prokaryotic and eukaryotic species (4-6). Structurally, TIR domains consist of alternating β strands and α helices (7-9). Upon recognition of either a PAMP or DAMP ligand, the ectodomains of stimulated TLRs form an M-shaped structure in which the C-termini of ectodomains converge, leading to dimerization of cytosolic TIR domains (7, 10-12). TIR dimerization exposes a composite binding site which provides a surface for recruitment of downstream TIR-domain containing adapter molecules present in the cytoplasm that, in turn, trigger signal propagation. Complementary surface areas of TIR domains, called interfaces, are key for the signal-initiated mutual recognition of TIR-containing proteins and the assembly of functional TLR signaling complexes through TIR:TIR domain interaction. TIR domains do not have a common TIR-binding motif and interact via structurally distinct regions.

Adapter protein recruitment to activated TLRs is exceptionally important as it governs the specificity of the TLR response (13). There are four recognized adapter proteins. Toll/interleukin-1 receptor domain-containing adapter protein (TIRAP), also known as MyD88-adapter-like (Mal), is a TIR domain-containing adapter utilized by both TLR2 and TLR4 to "bridge" MyD88 (a second adapter protein) to the receptors and, in turn, activate NF-κB (14-17). In the case of TLR4, there are two signaling pathways: MyD88-dependent and independent. The MyD88-dependent pathway utilizes TIRAP to bridge TLR4 and MyD88. The MyD88-independent pathway uses a third adapter protein, TRAM (TIR domain-containing adapter-inducing interferon-β- (TRIF-) related adapter molecule), which bridges TRIF (the fourth adapter protein) and allows for activation of IRF3. TIRAP appears to share a binding site with TRAM located at the TLR4 TIR homodimer (10, 11).

TIR domains, whether in the TLRs or the adapter proteins, mediate transient interactions of signaling proteins involved in inflammatory signaling and host defense. TIR domains tend to interact with other TIR domains, yet functional TIR:TIR interactions are specific, as exemplified by the recruitment of specific TIR-containing adapter proteins in response to activation of a particular receptor. Some TIR-containing adapter proteins participate in multiple signaling pathways, while others interact with a smaller set of proteins. For example, MyD88 is a necessary adapter for all members of the IL-1R family and all TLRs with the exception of TLR3, whereas TIRAP participates only in TLR2 and TLR4 signaling. Despite considerable effort, the molecular mechanisms that determine specificity of TIR:TIR interactions are not understood.

Small size (3-3.5 nm) and generally globular shape of TIR domains implies that any binary TIR:TIR complex has a limited interface size, typically less than 900 Å, and therefore a binary TIR complex is relatively weak and unstable. The stability of receptor complexes is achieved through a simultaneous, cooperative interaction of several (more than two) TIR domains, and multiple interface sites are expected in each TIR domain involved in signaling. Although the general mechanism of TLR signaling complex assembly is now commonly accepted, the architecture of TLR signaling complexes and the specific interface sites within TIR domains that mediate proteins interactions required for signaling complex assembly are not well understood.

Control of innate immunity in response to infection is vitally important as an impaired response increases susceptibility to infection, while an uncontrolled response can lead to inflammatory disease (2). TLRs and adapter proteins are important therapeutic targets because excessive TLR signaling is a pathogenic mechanism in many inflammatory diseases, including sepsis.

BRIEF SUMMARY OF INVENTION

The present invention defines linear epitopes/binding sites within TIR domains of TLRs and TLR adapter proteins that mediate TIR domain interactions required for assembly of TLR signaling complexes and TLR function. The key feature of these identified epitopes is that when a mimic of an epitope, such as a peptide or related molecule, is delivered to cells, it can block functional interactions of TIR domains through a competitive mechanism and, in some cases, inhibit signal transduction mediated by the TLR signaling complex.

In a first embodiment, the invention is drawn to TIR-derived decoy peptides. The TIR-derived decoy peptides block cellular signaling at low micromolar concentrations by mimicking a functional TIR epitope. The TIR-derived decoy peptides utilize a cell-permeating peptide to translocate the decoys across the cell membrane and into the cell. Thus, the TIR-derived decoy peptides are comprised of a cell-permeating peptide, such as the translocating segment of the *Drosophila* antennapedia homeodomain, fused to a TIR domain peptide.

In one aspect, the TIR-derived decoy peptides of the present invention are segments of the TIR domain of the TRAP adapter protein that are fused to the antennapedia homeodomain translocating segment. These TRAP based, TIR-derived decoy peptides include, but not limited to, TR3, TR5, TR6, TR9 and TR11, as defined herein (see Table 1).

In another aspect, the TIR-derived decoy peptides are segments of the TIR domain of the TRAM adapter protein that are fused to the antennapedia homeodomain translocating segment. These TRAM based, TIR-derived decoy peptides include, but not limited to TM4, TM4-ΔC and TM6 (see Table 1).

In another aspect, the TIR-derived decoy peptides are segments of the TIR domain of the TRIF adapter protein that are fused to the antennapedia homeodomain translocating segment. These TRIF based, TIR-derived decoy peptides include, but not limited to TF4, TF5 and TF5-AC (see Table 1).

In another aspect, the TIR-derived decoy peptides are segments of the TIR domain of the MyD88 adapter protein that are fused to the antennapedia homeodomain translocating segment. These MyD88 based, TIR-derived decoy peptides include, but not limited to M3, M4 and M5 (see Table 1).

In another aspect, the TIR-derived decoy peptides are segments of the TIR domain of TLR4 that are fused to the antennapedia homeodomain translocating segment. These TLR4 based, TIR-derived decoy peptides include, but not limited to 4R1, 4R3, 4R4/4BB, 4R9 and 4R11/4αE (see Table 1).

In another aspect, the TIR-derived decoy peptides are segments of the TIR domain of TLR2 that are fused to the antennapedia homeodomain translocating segment. These TLR2 based, TIR-derived decoy peptides include, but not limited to 2R1, 2R3, 2R9, 2BB, 2DD-αD (see Table 1).

In a second embodiment, the invention is drawn to TIR domain peptides. TIR domain peptides also mimic a functional TIR epitope but they are not fused to a cell-permeating peptide.

In one aspect, the TIR domain peptides of the present invention are segments of the TIR domain of TIRAP. These TIRAP based, TIR domain peptides include, but are not limited to, TR3a, TR5a, TR6a, TR9a, and TR11a, as defined herein (see Table 2).

In another aspect, the TIR domain peptides are segments of the TIR domain of the TRAM adapter protein. These TRAM based, TIR domain peptides include, but are not limited to, TM4a, TM4-ΔCa and TM6a (see Table 2).

In another aspect, the TIR domain peptides are segments of the TIR domain of the TRIF adapter protein. These TRIF based, TIR domain peptides include, but are not limited to, TF4a, TF5a and TF5-ΔCa (see Table 2).

In another aspect, the TIR domain peptides are segments of the TIR domain of the MyD88 adapter protein. These MyD88 based, TIR domain peptides include, but are not limited to, M3a, M4a and M5a (see Table 2).

In another aspect, the TIR domain peptides are segments of the TIR domain of TLR4. These TLR4 based, TIR domain peptides include, but are not limited to, 4R1a, 4R3a, 4R4/4BBa, 4R9a and 4R11/4αEa (see Table 2).

In another aspect, the TIR domain peptides are segments of the TIR domain of TLR2. These TLR2 based, TIR domain peptides include, but are not limited to, 2R1a, 2R3a, 2R9a, 2BBa, 2DD-αDa (see Table 2).

In a third embodiment, the invention is drawn to variants of the TIR-derived decoy peptides and the TIR domain peptides of the present invention. The variants are the TIR-derived decoy peptides and the TIR domain peptides of the present invention having one or two amino acid changes, whether substitutions, deletions or additions, to the amino acid sequence of the TIR-derived decoy peptide or the TIR domain peptide. The variants of the present invention maintain the activity of the unaltered version of the peptide.

In a fourth embodiment, the invention is drawn to methods of using the TIR-derived decoy peptides and the TIR domain peptides, and variants thereof, to alter inflammatory signaling and host defense pathways. In one aspect, the invention is drawn to methods of inhibiting TIR:TIR interaction between two TIR domain-bearing proteins comprising contacting a cell expressing TIR domain-bearing proteins with an effective amount of one or more of the TIR-derived decoy peptides and the TIR domain peptides, and variants thereof, of the present invention. In a particular aspect, the invention is drawn to methods of inhibiting TIR:TIR interaction between two TIR domain-bearing proteins comprising contacting a cell expressing TIR domain-bearing proteins with an effective amount of one or more of the TIR-derived decoy peptides, and variants thereof.

In another aspect, the invention is drawn to methods of inhibiting TLR activation comprising contacting a cell expressing TLRs with an effective amount of one or more of the TIR-derived decoy peptides and the TIR domain peptides, and variants thereof, of the present invention. In a particular aspect, the invention is drawn to methods of inhibiting TLR activation comprising contacting a cell expressing TLRs with an effective amount of one or more of the TIR-derived decoy peptides, and variants thereof.

In another aspect, the invention is drawn to methods of inhibiting TLR-mediated signaling comprising contacting a cell expressing TLRs with an effective amount of one or more of the TIR-derived decoy peptides and the TIR domain peptides, and variants thereof, of the present invention. In a particular aspect, the invention is drawn to methods of inhibiting TLR-mediated signaling comprising contacting a cell expressing TLRs with an effective amount of one or more of the TIR-derived decoy peptides, and variants thereof.

In relevant aspects of this embodiment, the TIR domain-bearing proteins are TLRs, or TLR adapter proteins, or both. The TLRs may be any TLR, for example, but not limited, one or more receptors selected from the group consisting of TLR1, TLR2, TLR3, TLR4, TLR5, TLR6, TLR7, TLR8, TLR9, TLR10, TLR11, TLR12, and TLR13. In a preferred aspect, the TLR is TLR2 or TLR4, or both. The TLR adapter protein may be any TLR adapter protein, for example, but not limited to, one or more proteins selected from the group consisting of TIRAP, MyD88, TRIF, and TRAM. In exemplary aspects, the one or more TIR-derived decoy peptides are selected from the group consisting of TR3, TR5, TR6, TR9 and TR11.

In a fifth embodiment, the invention is drawn to methods of treating a subject having a condition mediated by TLR signaling comprising administering to a subject in need thereof a therapeutically-effective amount of a pharmaceutical composition comprising one or more of the TIR-derived decoy peptides and the TIR domain peptides, and variants thereof, of the present invention and a pharmaceutically acceptable carrier or diluent. In a particular aspect, the invention is drawn to methods of treating a subject having a condition mediated by TLR signaling comprising administering to a subject in need thereof a therapeutically-effective amount of a pharmaceutical composition comprising one or more of the TIR-derived decoy peptides, and variants thereof, and a pharmaceutically acceptable carrier or diluent. In exemplary aspects, the one or more TIR-derived decoy peptides are selected from the group consisting of TR3, TR5, TR6, TR9 and TR11. In aspects of this embodiment, the condition mediated by TLR signaling may be, but is not limited to, inflammation, septic shock, or a inflammatory or genetic disease promoted by excessive TLR activation.

In a sixth embodiment, the invention is drawn to methods of treating a subject having septic shock or other inflammatory condition comprising administering to a subject in need thereof a therapeutically-effective amount of a pharmaceutical composition comprising one or more of the TIR-derived decoy peptides and the TIR domain peptides, and variants thereof, of the present invention and a pharmaceutically acceptable carrier or diluent. In a particular aspect, the invention is drawn to methods of treating a subject having septic shock or other inflammatory condition comprising administering to a subject in need thereof a therapeutically-effective amount of a pharmaceutical composition comprising one or more of the TIR-derived decoy peptides, and variants thereof, and a pharmaceutically acceptable carrier or diluent. In exemplary aspects, the one or more TIR-derived decoy peptides are selected from the group consisting of TR3, TR5, TR6, TR9 and TR11.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits of this invention.

BRIEF DESCRIPTION OF DRAWINGS

FIG. 3C. IL-6 and TNF-α were measured by ELISA in macrophage supernatants collected 5 h after P3C (500 ng/ml) stimulation. FIG. 3D. Peptides TR3 and TR6 inhibit ERK activation induced by TLR2 agonist, P3C. ERK phosphorylation was measured by Western analysis in primary macrophage stimulated by P3C for 30 min.

FIG. 5A and FIG. 5B. Peritoneal macrophages were pre-incubated with 5 or 20 µM of control or decoy peptides for 30 min prior to stimulation with LPS (100 ng/ml). Cells were lysed 1 (panel FIG. 5A) or 5 h (panel FIG. 5B) after LPS challenge. Cytokine mRNA expression is normalized to the expression of the housekeeping gene, Hprt. Data represent the means±s.e.m. of 4 independent experiments. Asterisks indicate data statistically different from the control group ($p<0.001$). FIG. 5C and FIG. 5D. Cell lysates for immunoblotting was obtained 30 min (FIG. 5C) or 2 h (FIG. 5D) after LPS stimulation. GAPDH was used as a loading control. Panels FIG. 5C and FIG. 5D show a representative blot of 4 separate experiments.

(FIG. 7G) The residues that are conserved in TRAM and TIRAP peptides are underlined. The mMyD88 amino acid sequence is found in SEQ ID NO:83. The mTIRAP amino acid sequence is found in SEQ ID NO:27. The mTRIF amino acid sequence is found in SEQ ID NO:84. The mTRAM amino acid sequence is found in SEQ ID NO:32.

FIG. 8A and FIG. 8C. Effects of various modifications of TM4 peptide on TLR4-driven activation of MAPKs. FIG. 8B and FIG. 8D. Effects of various modifications of TM4 peptide on TLR4-driven expression of cytokine mRNA. Data show that the N-terminal and middle parts of TM4 are important for inhibition because peptides that contain these segments retain inhibitory activity. The amino acid sequence of "C" in FIG. 8A is found in SEQ ID NO:68. The amino acid sequence of "M" in FIG. 8A is found in SEQ ID NO:67. The amino acid sequence of "N" in FIG. 8A is found in SEQ ID NO:66. The amino acid sequence of "R4" in FIG. 8A is found in SEQ ID NO:30. The amino acid sequence of "E/A" in FIG. 8A is found in SEQ ID NO:71. The amino acid sequence of "P/H" in FIG. 8A is found in SEQ ID NO:72. The amino acid sequence of "C/H" in FIG. 8A is found in SEQ ID NO:73. The amino acid sequence of "R4" in FIG. 8C is found in SEQ ID NO:30. The amino acid sequence of "ΔN" in FIG. 8C is found in SEQ ID NO:31. The amino acid sequence of "AM" in FIG. 8C is found in SEQ ID NO:69. The amino acid sequence of "AC" in FIG. 8C is found in SEQ ID NO:70.

(FIG. 9A) A total of $6 \times 10^5$ HEK293T cells was transfected with 1 μg pcDNA3.1-mTLR4-Cer and pEF-BOS-mTRAM-HA. Twenty-four hours posttransfection, the cells were treated with 20 μM of each peptide for 1 h. Cell lysates were immunoprecipitated with anti-GFP Ab and blotted with anti-HA-HRP. (FIG. 9B) A total of $2 \times 10^6$ mouse peritoneal macrophages was pretreated with 20 μM of each peptide for 30 min prior to stimulation with 100 ng/ml LPS. Cell extracts were obtained 30 min after LPS treatment, immunoprecipitated with goat anti-TLR4 Ab, and blotted with rabbit anti-MyD88 or anti-TLR4 Ab. Data are representative of three independent experiments.

(FIGS. 10A-10E) C57BL/6J mice were injected i.p. with purified *Escherichia coli* K235 LPS (1 μg/g) or PBS. Peptides (10 nmol/g of animal weight) were injected i.p. (FIG. 10A, FIG. 10B, FIG. 10D, FIG. 10E) or i.v. (FIG. 10C) 1 h before (FIG. 10A, FIG. 10B, and FIG. 10C) or 30 min after (FIG. 10D, FIG. 10E) i.p. injection of LPS. Data in panels FIG. 10A and FIG. 10D show plasma IL-6 and TNF-α levels measured 2 h after LPS challenge. Peptide TM8/9 was used as a non-inhibitory control peptide. Data represent the means±s.e.m. for 6-12 blood samples obtained in at least three independent experiments. *p<0.01. (FIG. 10F, FIG. 10G) C57BL/6J mice were challenged i.p. with a lethal LPS dose (17.5 μg/g). Peptides (10 nmol/g) were injected i.p. 1 h before LPS challenge. Panel FIG. 10G also shows survival in the group treated with TM4-ΔC 3 h after LPS challenge (n=7). The statistical significance of changes in mortality and survival time was determined by the Mantel Cox log-rank test using GraphPad Prism software (Version 5.04). *p<0.01.

FIG. 11A and FIG. 11B. Effects of TRIF-derived peptides on LPS-induced expression of TNF-α, IL-1β, IFNβ, and RANTES mRNA. Peritoneal macrophages were treated with 5 or 20 μM of TRIF-derived decoy peptides for 30 minutes, and then stimulated with LPS for 1 (FIG. 11A and FIG. 11B) or 5 (FIG. 11C) hour. Cytokine mRNA expression was measured 1 (FIG. 11A, FIG. 11B) or 5 h (FIG. 11C) after LPS challenge by Real-time RT-PCR, and is normalized to the expression of HPRT housekeeping gene. Data show means and SEM of 4 independent experiments. *p<0.001. FIG. 11D and FIG. 11E. Cell lysates for immunoblotting was obtained 30 min (FIG. 11D) or 2 h (FIG. 11E) after LPS stimulation. GAPDH and total STAT1 were used as loading controls.

FIG. 13A. Effects of MyD88-derived peptides on LPS-induced expression of TNF-α and IL-1β mRNA. Mouse peritoneal macrophages were treated with 20 μM of MyD88-derived decoy peptides for 30 minutes, and stimulated with LPS for 1 hour (FIG. 13A) 30 minutes (FIG. 13B). FIG. 13B. Effect of MyD88 decoy peptides on activation of p-38, JNK, and ERK MAPKs. Cells were pretreated with peptides at 20 μM for 30 minutes and stimulated with 100 ng/ml LPS for additional 30 min.

(FIG. 15A) Peptides 2R1, 2R3, and 2R9 inhibit cytokine mRNA expression induced by triacylated lipopeptide, S-[2,3-bis(palmitoyloxy)-(2-RS)-propyl]-N-palmitoyl-(R)-Cys-Ser-Lys4-OH (P3C) that activates TLR2/1 heterodimer. (FIG. 15B) Peptides 2R1 and 2R9 inhibit cytokine mRNA expression induced by diacylated lipopeptide, S-[2,3-bis(palmitoyloxy)-(2-RS)-propyl]-[R]-Cys-Ser-Lys4-OH (P2C), a TLR agonist that activates the TLR2/TLR6 heterodimer. Macrophage were pretreated with decoy peptides at indicated concentration for 30 min and then stimulated with a TLR2 agonist for 1 hour. P3C and P2C were used at 500 and 50 ng/ml, respectively.

(FIG. 16A). Peptide 2BB inhibits IL-1β expression induced by TLR2 agonists. (FIG. 16B). Peptide 2DD-αD potently inhibits TLR2-driven IL-1β expression. (FIG. 16C). Peptide 2R9 strongly inhibits TLR2-induced ERK activation.

DETAILED DESCRIPTION OF THE INVENTION

I. Definitions

Figure 1:
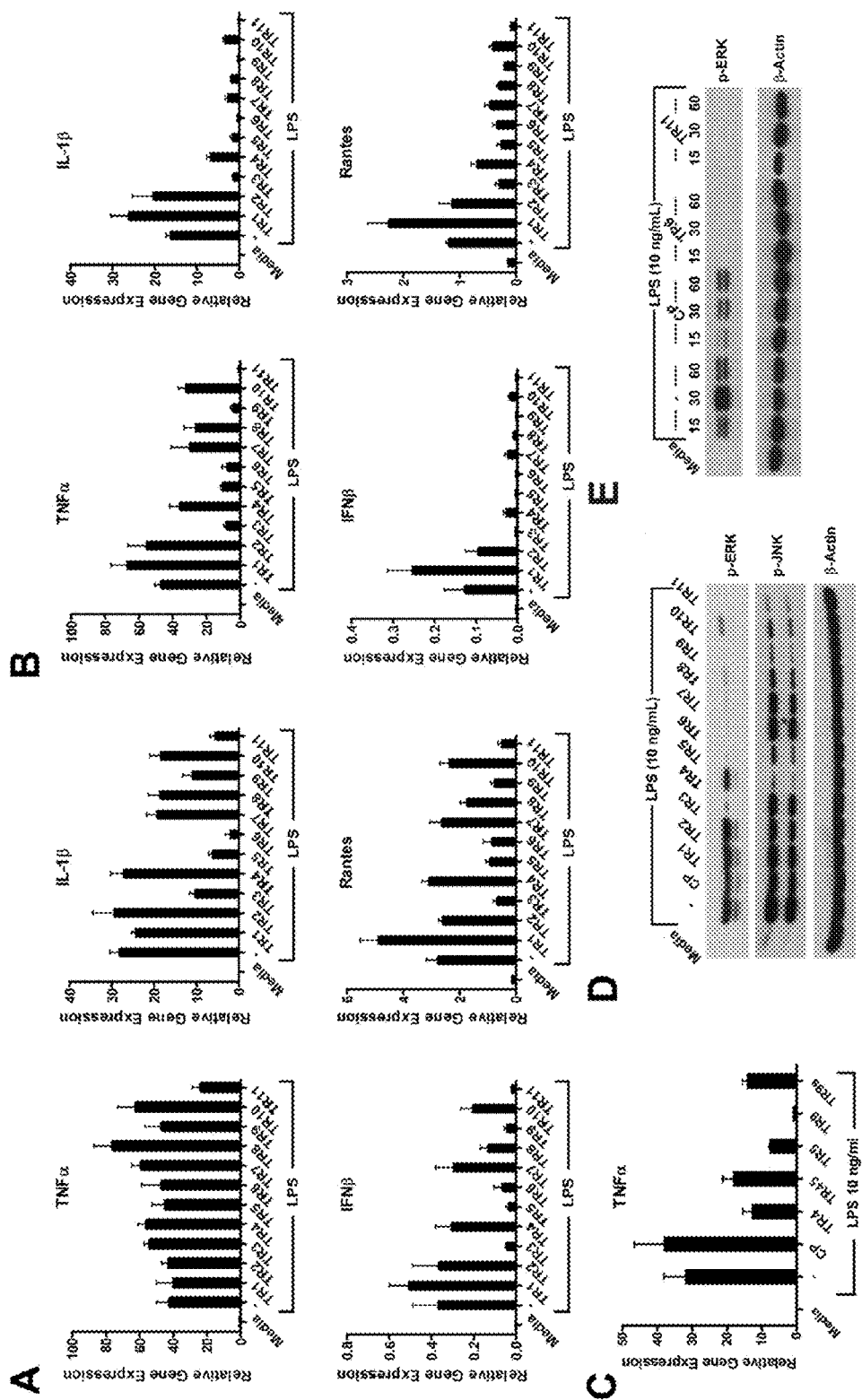
FIG. 1. Effects TRAP TIR-derived decoy peptides on LPS-induced cytokine mRNA expression (FIG. 1A, FIG. 1B, and FIG. 1C) and MAPK activation (FIG. 1D and FIG. 1E). Mouse macrophages were incubated in the presence of 5 µM (FIG. 1A) or 20 µM (FIG. 1B-1E) decoy peptide for 30 min prior to stimulation with LPS (10 ng/ml). Cytokine mRNA expression was measured 1 h after LPS challenge and is normalized to the expression of HPRT gene. mRNA expression data show mean and SEM for 6 separate experiments. Protein extracts for Western analysis were taken 30 min after LPS stimulation (FIG. 1D). Each Western blot image is representative of 4 separate experiments.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more than one. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "treat", "treating" and "treatment" have their ordinary and customary meanings, and include one or more of: ameliorating a symptom of a disease or condition; blocking or ameliorating a recurrence of a symptom of a disease or condition; decreasing in severity and/or frequency a symptom of a disease or condition; slowing, interrupting, arresting, controlling, or stopping the progression of a disease or condition. The terms do not necessarily indicate a total elimination of the disease or condition, or a symptom of the disease or condition. Treatment means ameliorating, blocking, reducing, decreasing or inhibiting by about 1% to about 100% versus a subject to which the peptides of the present invention have not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which the peptides have not been administered.

II. The Present Invention

TLR signaling is a significant therapeutic target because uncontrolled TLR signaling is a pathogenic mechanism in many inflammatory diseases, including septic shock. Molecules that can block the TLR signaling cascade would be helpful in treating subjects exhibiting a disregulated immune response. The present invention is directed to such molecules.

Thus, the present invention provides novel peptides that function as decoys to block the assembly of TLR signaling complexes that occurs through TIR domain interaction. TIR: TIR recognition and binding forms the basis for TLR signaling. The novel peptides comprise segments from the TIR domains of TLRs and TLR adaptor proteins as the basis for the decoy peptides. These segments are fused to a cell-permeating peptide to produce the TIR-derived decoy peptides of the present invention.

Suitable cell-permeating peptides include the translocating segment of *Drosophila* antennapedia homeodomain (RQIKIWFQNRRMKWKK; SEQ ID NO:50). Other suitable cell-permeating peptides include Herpes simplex virus 1 (HSV-1) protein VP22 and trans-activating transcriptional activator (Tat) from HIV-1. While the examples provide herein place the cell-permeating peptide at the amino terminal end of the decoy peptides, depending on the identity of the cell-permeating peptide it may also be placed at the carboxy terminus of the decoy peptides.

The TIR-derived decoy peptides of the present invention include those based on segments of the TIRAP adapter protein. These TIR-derived decoy peptides comprise (i) the antennapedia peptide (RQIKIWFQNRRMKWKK; SEQ ID NO:50) fused to (ii) segments of the TRAP TIR domain. These decoy peptides are set forth in Table 1. As discussed herein, all of these TIRAP-derived decoy peptides have the ability to inhibit LPS signaling through TLR4, while two of these TIRAP peptides have the ability to inhibit P3C signaling through TLR2.

The TIR-derived decoy peptides of the present invention include those based on segments of the TRAM adapter protein. These TIR-derived decoy peptides comprise (i) the antennapedia peptide (RQIKIWFQNRRMKWKK; SEQ ID NO:50) fused to (ii) segments of the TRAM TIR domain. These decoy peptides are set forth in Table 1. These TIR-derived decoy peptides generally target the TLR4 and TLR2 signaling pathway.

The TIR-derived decoy peptides of the present invention include those based on segments of the TRIF adapter protein. These TIR-derived decoy peptides comprise (i) the antennapedia peptide (RQIKIWFQNRRMKWKK; SEQ ID NO:50) fused to (ii) segments of the TRIF TIR domain. These decoy peptides are set forth in Table 1. These TIR-derived decoy peptides generally target the TLR4 signaling pathway.

The TIR-derived decoy peptides of the present invention include those based on segments of the MyD88 adapter protein. These TIR-derived decoy peptides comprise (i) the antennapedia peptide (RQIKIWFQNRRMKWKK; SEQ ID NO:50) fused to (ii) segments of the MyD88 TIR domain. These decoy peptides are set forth in Table 1. These TIR-derived decoy peptides generally target the TLR4 signaling pathway.

The TIR-derived decoy peptides of the present invention include those based on segments of TLR4. These TIR-derived decoy peptides comprise (i) the antennapedia peptide (RQIKIWFQNRRMKWKK; SEQ ID NO:50) fused to (ii) segments of TLR4. These decoy peptides are set forth in Table 1. These TIR-derived decoy peptides generally target the TLR4 and TLR2 signaling pathways, while some may target TLR2.

The TIR-derived decoy peptides of the present invention include those based on segments of TLR2. These TIR-derived decoy peptides comprise (i) the antennapedia peptide (RQIKIWFQNRRMKWKK; SEQ ID NO:50) fused to (ii) segments of TLR2. These decoy peptides are set forth in Table 1. These TIR-derived decoy peptides generally target the TLR2 signaling pathway.

TABLE 1

Functional epitopes of TIR domains of TLRs and TLR adapter proteins.

Figure 4:
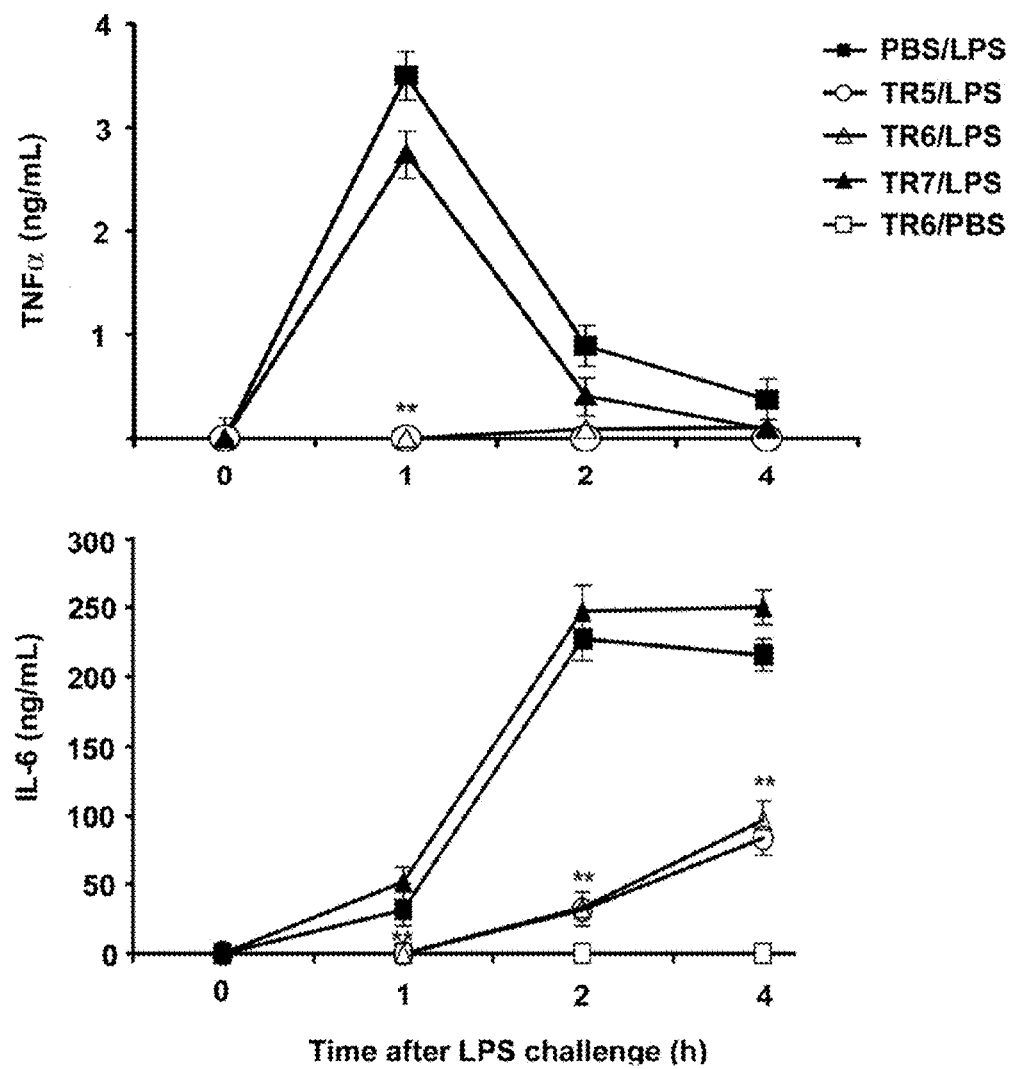
FIG. 4. Effect of select TRAP decoy peptides on TNF-α (upper panel) and IL-6 (lower panel) in blood following an ip LPS challenge. C57BL/6J mice were injected with TR5, TR6, or TR7 peptide or mock-treated 1 hour before injection of purified E. coli LPS. Peptides and LPS were injected to mice intraperitonealy 10 nmol or 1 µg per gram of animal weight, correspondingly.
Figure 11:
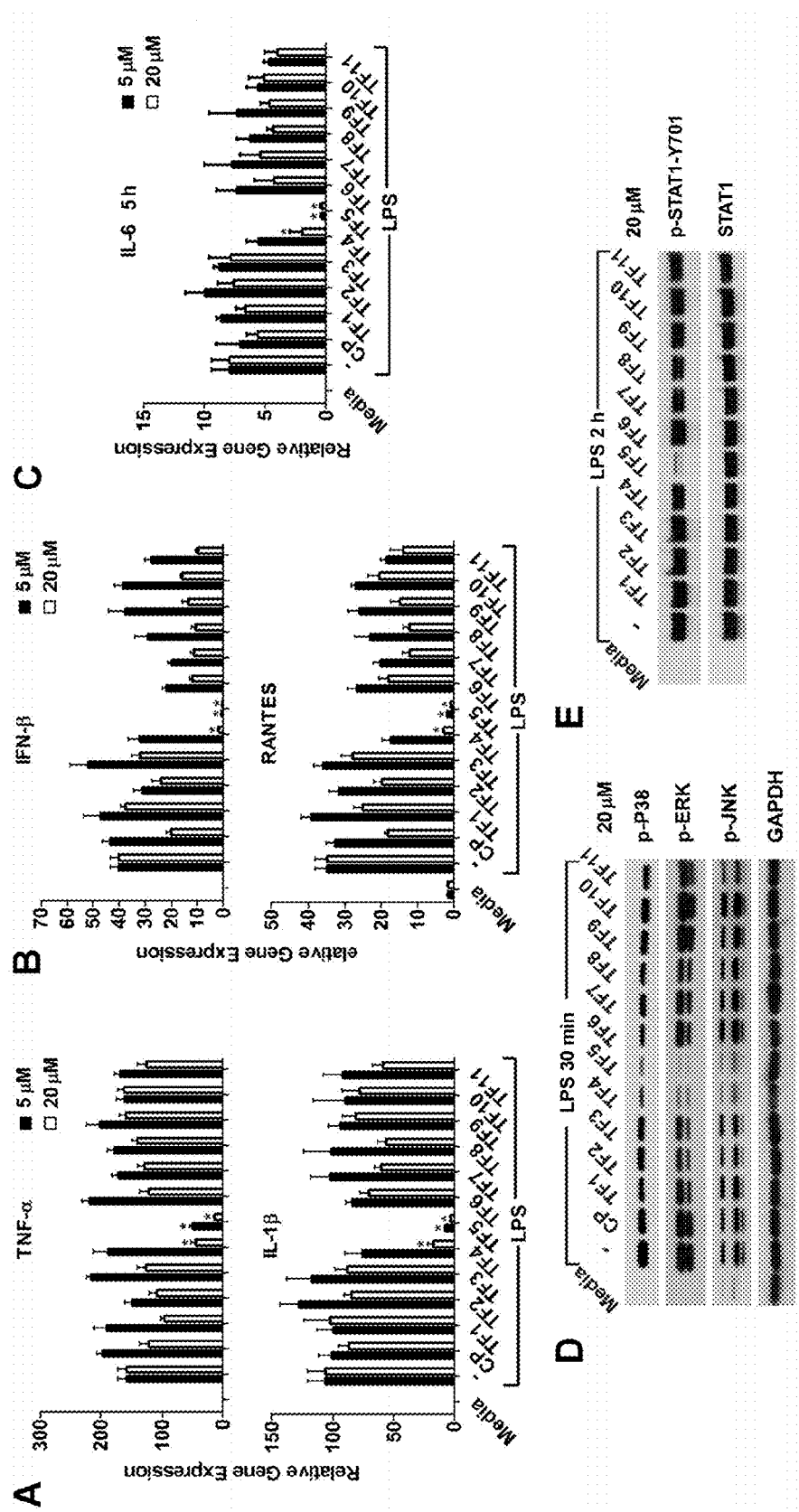
FIG. 11. TRIF TIR-derived peptides, TF4 and TF5, inhibit the TLR4-induced cytokine mRNA expression (FIG. 11A, FIG. 11B, and FIG. 11C), and MAPK and STAT1 activation (FIG. 11D and FIG. 11E).
Figure 12:
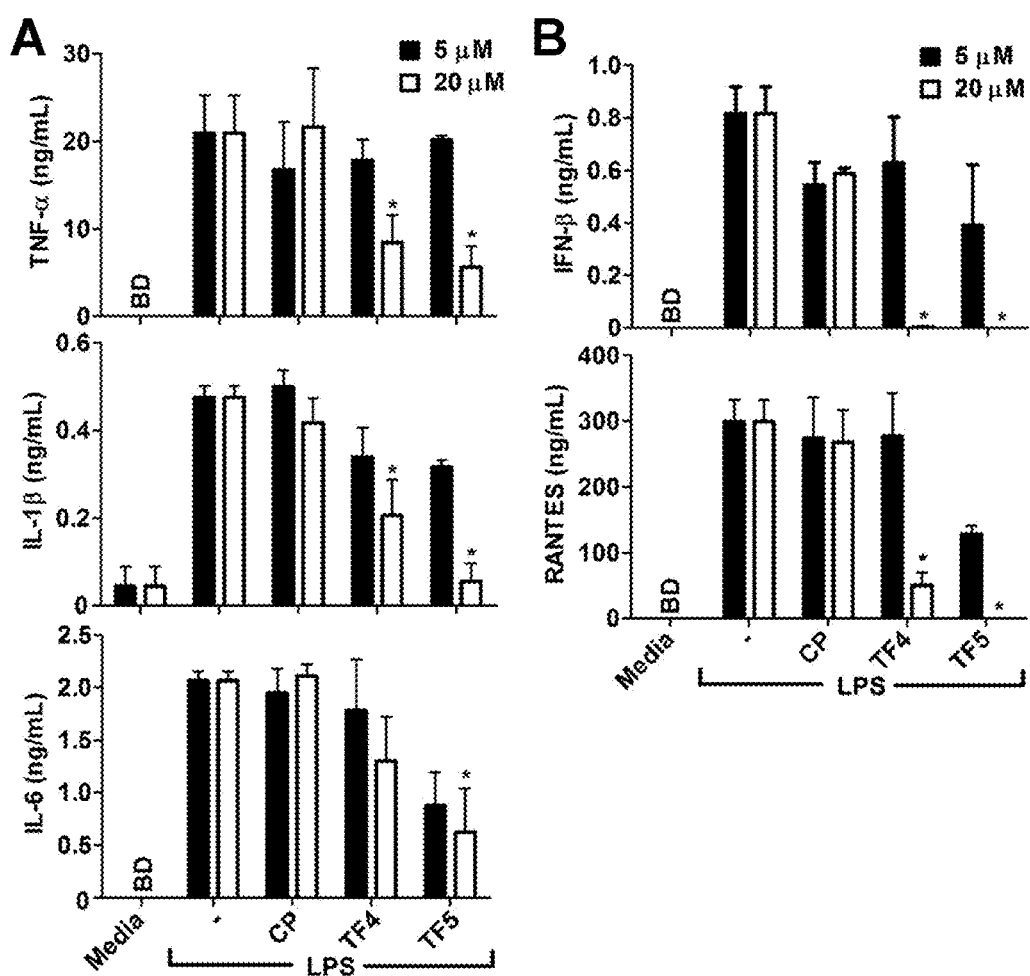
FIG. 12. TF5 and TF4 inhibit LPS-induced cytokine secretion. Peritoneal macrophages were pre-incubated with 5 or 20 μM of indicated TRIF peptide for 30 min prior to stimulation with LPS (100 ng/ml). Supernatants were collected 24 h later and analyzed for MyD88-dependent (TNF-α, IL-1β, and IL-6) (FIG. 12A), or TRIF-dependent (IFN-β and RANTES) (FIG. 12B) cytokine production. Data represent the means±SEM of 3 independent experiments. *p<0.01. BD.—below detection limit.
Figure 17:
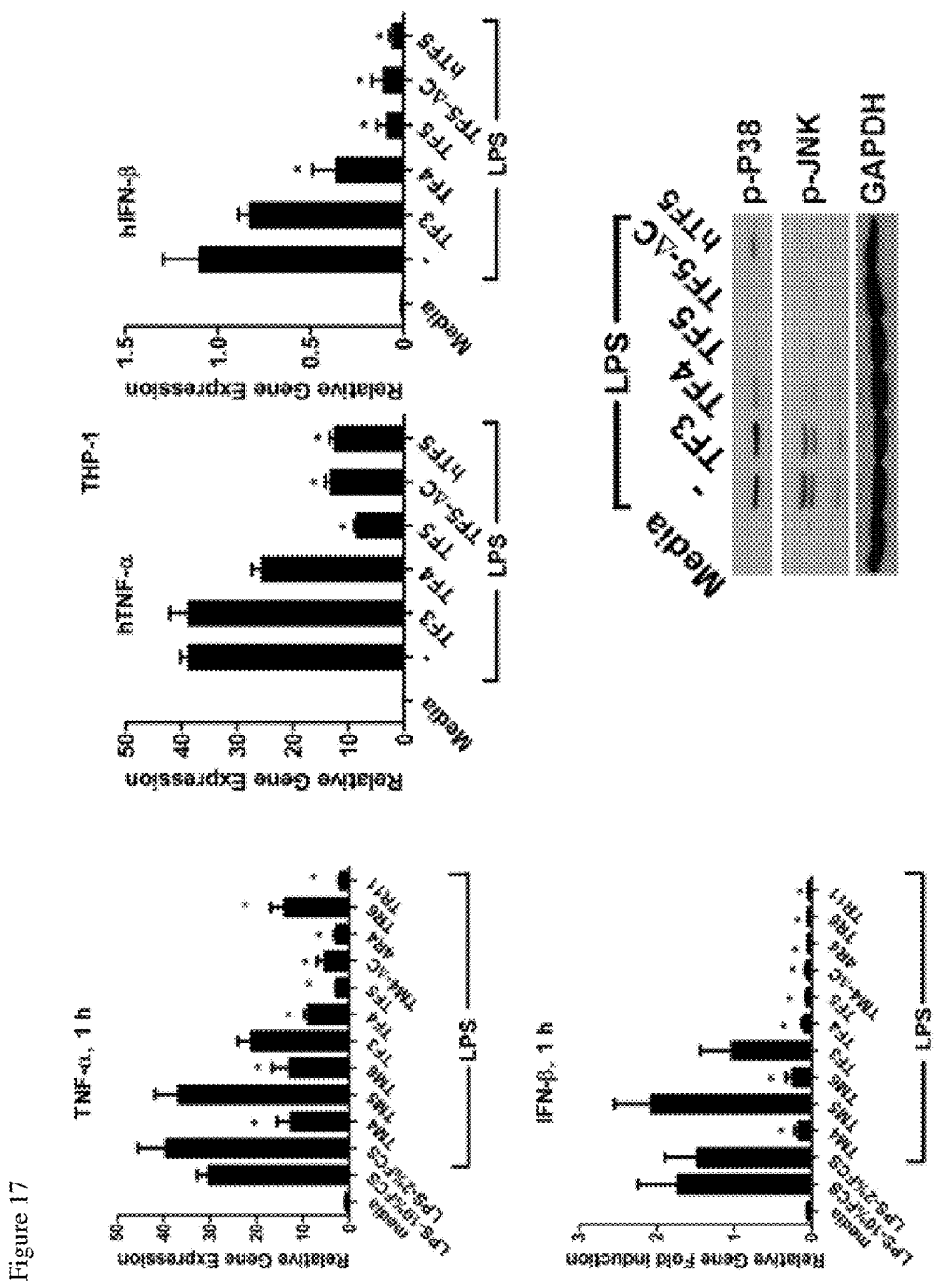
FIG. 17. Select TIR-derived peptides inhibit TLR4-induced TNF-α and IFN-β mRNA expression and MAPK activation in THP-1 cells. Peptides were used at 20 μM. Cells were stimulated with 100 ng/ml LPS for 1 hour. Each decoy peptide was synthesized in tandem with the Antennapedia homeodomain cell-permeating sequence.

| Peptide name | Sequence SEQ ID NO: | Prototype protein - main structural element | Supporting evidence | In vivo efficiency | Human/mouse identity/similarity | Species specificity[1] | Ref. | Effective conc. [μM][2] | Targeted TLR pathway(s) | Protein target/binding partner[3] |
|---|---|---|---|---|---|---|---|---|---|---|
| TIRAP BASED, TIR-DERIVED DECOY PEPTIDES | | | | | | | | | | |
| TR3 | RQIKIWFQNRRMKWKK[4] EGSQASLRCF SEQ ID NO: 1 | AB loop and a part of strand B | FIG. 1, 2, 3 | ND[5] | | m | (30) | 20 - TLR4 40 - TLR2 | TLR4; TLR2 | Multiple TIR domains |
| TR5 | RQIKIWFQNRRMKWKK ELCQALSRSHCR SEQ ID NO: 2 | Second helical region of TIRAP TIR (helix B) | FIG. 1, 2, 4 | yes, i.p. FIG. 4 | 91%/91% | m (R/S) | (30) | 20 | TLR4 | ND |
| TR6 | RQIKIWFQNRRMKWKK PGFLRDPWCKYQML SEQ ID NO: 3 | Third helical region of TIRAP TIR (helix C) | FIG. 1, 2, 3, 4, 7, 9, 10, 17 | yes, i.p. FIG. 4, 10 | 93% | m, ferret, (h and many R/Q) and FIG. 17 | (30) | 20 - TLR4 40 - TLR2 | TLR4; TLR2 | MyD88; TRIF |
| TR9 | RQIKIWFQNRRMKWKK AAYPPELRFMYYVD SEQ ID NO: 4 | Fourth helical region of TIRAP TIR (helix D) | FIG. 1, 2 | ND | 100% | h, m, rabbit | (30) | 20 | TLR4 | ND |
| TR11 | RQIKIWFQNRRMKWKK GGFYQVKEAVIHY SEQ ID NO: 5 | Fifth helical region of TIRAP TIR (helix E) | FIG. 1, 2, 17 | ND | 77%/77% | ND | (30) | 20 | TLR4 | ND |
| TRAM BASED, TIR-DERIVED DECOY PEPTIDES | | | | | | | | | | |
| TM4 | RQIKIWFQNRRMKWKK IVFAEMPCGRLHLQ SEQ ID NO: 6 | BB loop of TRAM TIR | FIG. 5, 6, 7, 8, 9, 10, 12, 17 | yes, i.p. and i.v. FIG. 17 | 86%/92% | h, m, bovine, pig, and other. (FIG. 17) | (19, 31) | 10 | TLR4 | ND This peptide includes TM4-ΔC |
| TM4-ΔC | RQIKIWFQNRRMKWKK IVFAEMPCG SEQ ID NO: 7 | Truncated BB loop of TRAM TIR | FIG. 8, 9, 10, 17 | yes, i.p. and i.v. FIG. 17 | 89%/100% | h, m, bovine, pig, and other. (FIG. 17) | (31) | 10 | TLR4 | ND |
| TM6 | RQIKIWFQNRRMKWKK ENFLRDTWCNFQFY SEQ ID NO: 8 | Third helical region of TRAM TIR (helix C) | FIG. 5, 6, 7, 9, 10, 17 | yes, i.p. FIG. 11 | 100% | m, h (FIG. 17) | (31) | 20 | TLR4 | TRIF; MyD88 |
| TRIF BASED, TIR-DERIVED DECOY PEPTIDES | | | | | | | | | | |
| TF4 | RQIKIWFQNRRMKWKK CEEFQVPGRGELH SEQ ID NO: 9 | BB loop of TRIF TIR | FIG. 11, 12, 17 | ND | 92%/100% | m (FIG. 17) | — | 20 | TLR4 | ND |
| TF5 | RQIKIWFQNRRMKWKK CLQDAIDHSGFT SEQ ID NO: 10 | Second helical region of TRIF TIR (helix B) | FIG. 11, 12, 17 | Yes, i.p. | 83% | m, (h G/A) (FIG. 17) | — | 20 | TLR4 | A shorter version of this peptide, TF5-ΔC, has similar inhibitory activity. |
| TF5-ΔC | RQIKIWFQNRRMKWKK CLQDAIDHS SEQ ID NO: 11 | Second helical region of TRIF TIR (helix B) | FIG. 17 | Yes, i.p. | 100% | h, m, ferret, Guinea pig, primates (FIG. 17) | — | 20 | TLR4 | ND |
| MYD88 BASED, TIR-DERIVED DECOY PEPTIDES | | | | | | | | | | |
| M3 | RQIKIWFQNRRMKWKK EQTDYRLKLC SEQ ID NO: 12 | AB loop and a part of strand B. | FIG. 13 | ND | 90%/100% | m, (h D/N) | — | 20 | TLR4 | ND |
| M4 | RQIKIWFQNRRMKWKK SDRDVLPGTCVWS | BB loop | FIG. 13 | ND | 100% | h, m, sheep, horse, dog, | (19, 32) | 20 | TLR4 | ND |

TABLE 1-continued

Functional epitopes of TIR domains of TLRs and TLR adapter proteins.

Figure 13:
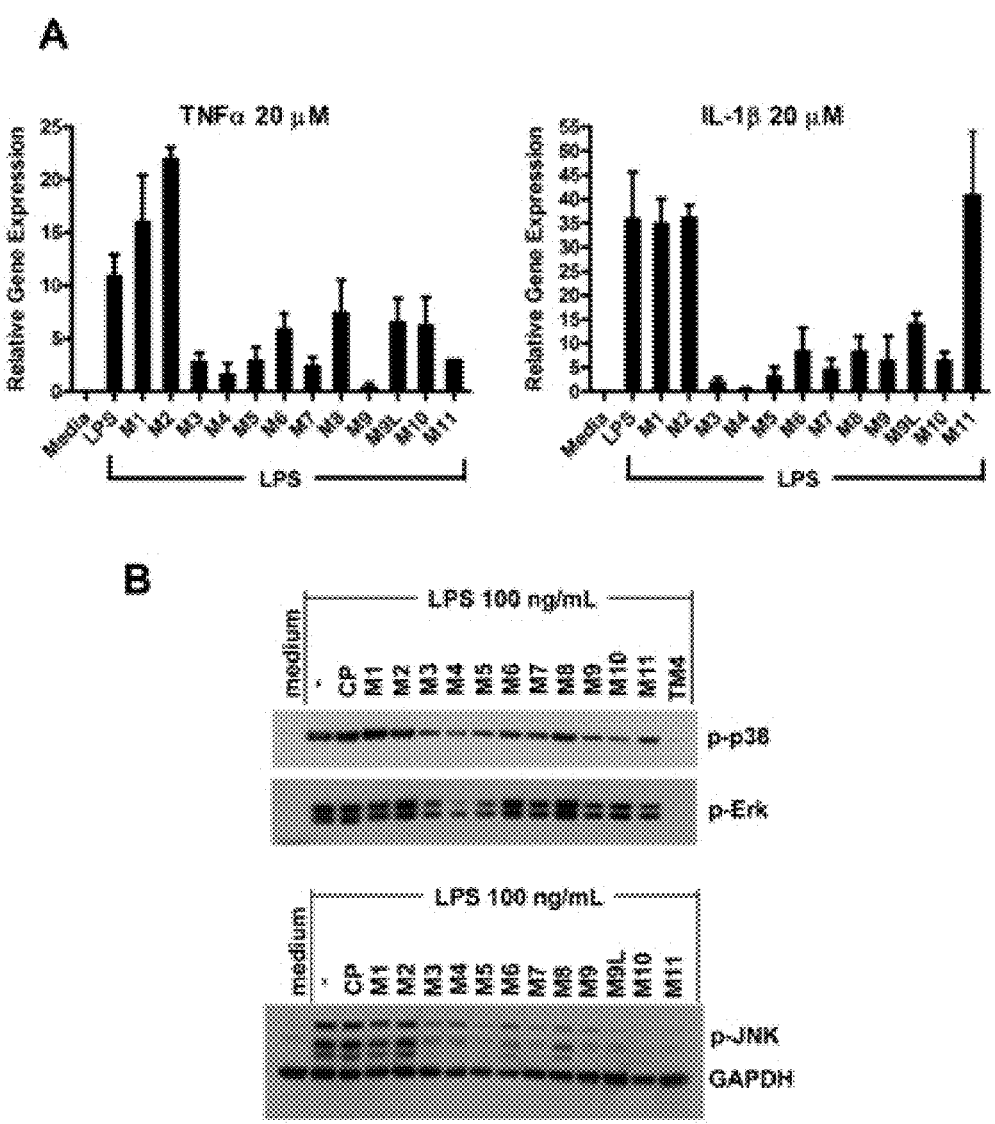
FIG. 13. MyD88 TIR-derived peptides M3, M4, and M5 inhibit TLR4-induced cytokine mRNA expression (FIG. 13A), and activation of ERK and p38 MAPK (FIG. 13B).
Figure 14:
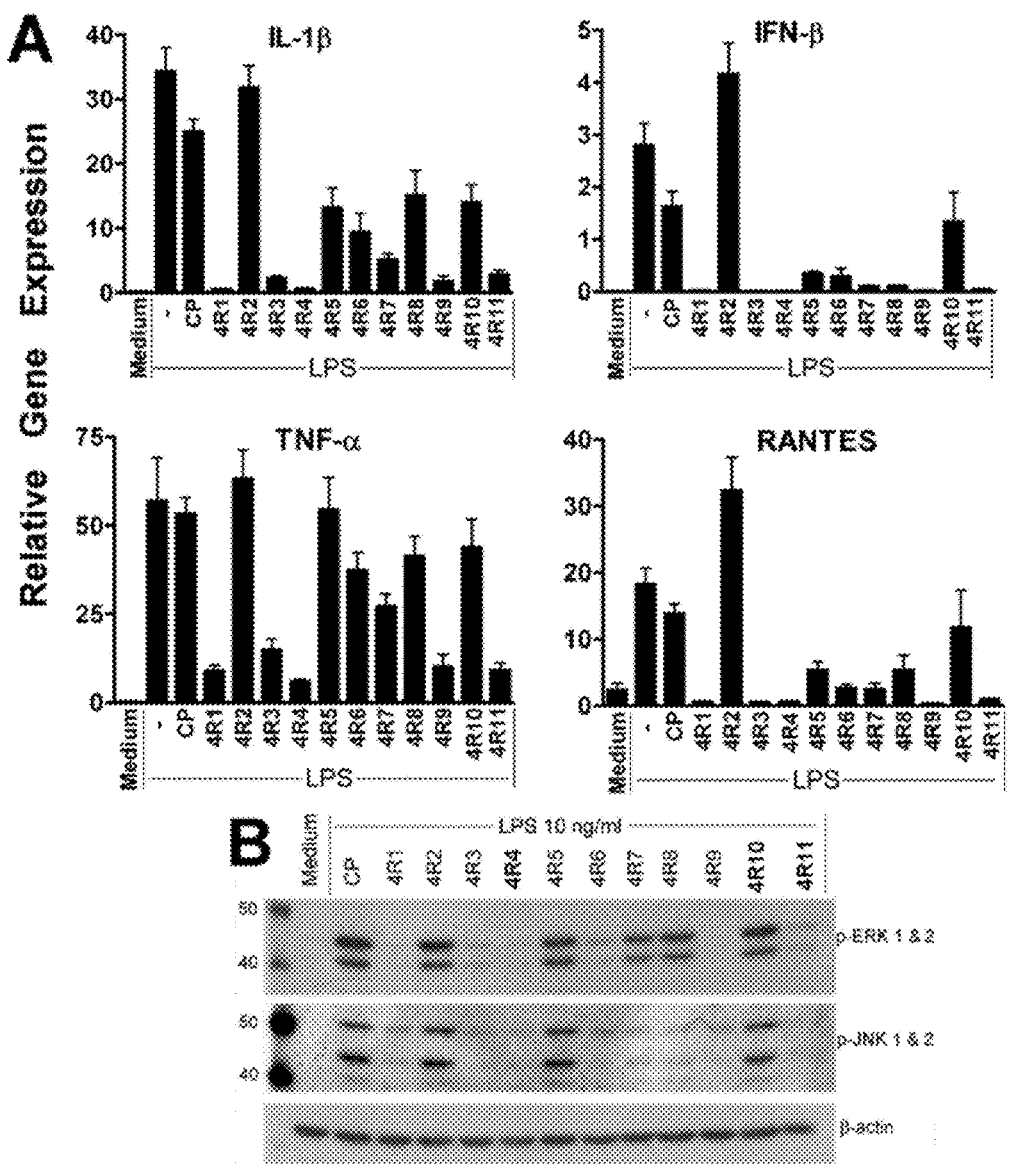
FIG. 14. Effects of TLR4 TIR-derived peptides on cytokine mRNA expression (FIG. 14A) and MAPK activation (FIG. 14B) induced by lipopolysaccharide (LPS), a potent TLR4 agonist, in peritoneal macrophages. Peptides 4R1, 4R3, 4BB, 4R9, and 4αE potently inhibit cytokine mRNA induction and activation of ERK and JNK MAPKs. Sequences of inhibitory peptides are shown in Table 1.
Figure 15:
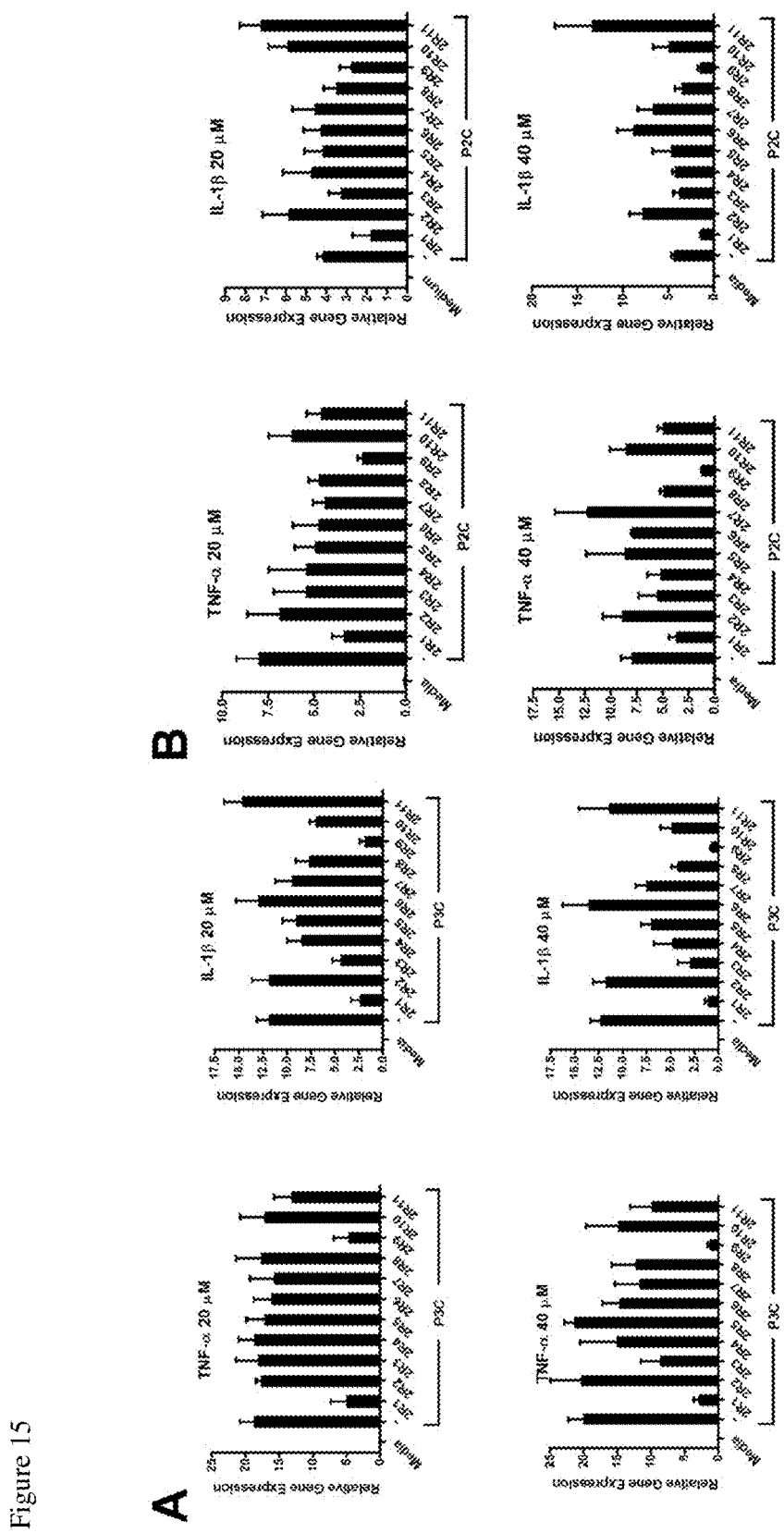
FIG. 15. Effects of TLR2 TIR-derived decoy peptides on cytokine mRNA expression induced by TLR2 agonists, P3C (FIG. 15A) and P2C (FIG. 15B).
Figure 16:
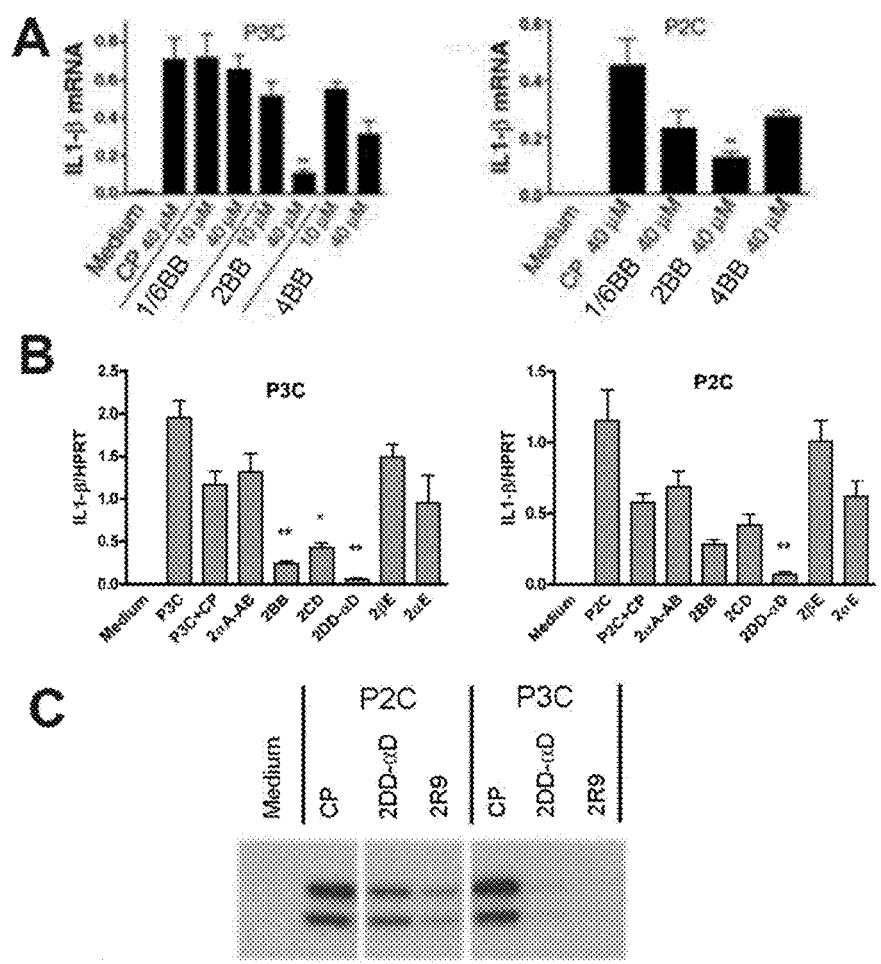
FIG. 16. Effects of TLR2 TIR-derived peptides on signaling induced by TLR2 agonists, P2C and P3C.

| Peptide name | Sequence SEQ ID NO: | Prototype protein - main structural element | Supporting evidence | In vivo efficiency | Human/mouse identity/similarity | Species specificity[1] | Ref. | Effective conc. [µM][2] | Targeted TLR pathway(s) | Protein target/binding partner[3] |
|---|---|---|---|---|---|---|---|---|---|---|
| | SEQ ID NO: 13 | Second helical region of MyD88 TIR (helix B) | FIG. 13 | ND | 100% | bovine, pig, chicken and others | — | 20 | TLR4 | ND |
| M5 | RQIKIWFQNRRMKWKK IASELIEKRCRRM SEQ ID NO: 14 | | | | | | | | | |
| | | | | | | TLR4 BASED, TIR-DERIVED DECOY PEPTIDES | | | | |
| 4R1 | RQIKIWFQNRRMKWKK AGCKKYSRGESIYD SEQ ID NO: 15 | TLR4. Linker to transmembrane region | FIG. 14 | ND | | h, m, rat, bovine, and other species | (1) | 20 | TLR4 | TLR4 (1) |
| 4R3 | RQIKIWFQNRRMKWKK EEGVPRFHLC SEQ ID NO: 16 | AB loop and part of strand B. | FIG. 14 | ND | | h, m, rat, bovine, pig, dog, and other species | — | 20 | TLR4 | ND |
| 4R4/4BB | RQIKIWFQNRRMKWKK LHYRDFIPGVAIAA SEQ ID NO: 17 | BB loop of TLR4 TIR | FIG. 14 | ND | 100% | h, m, rat, bovine, pig, dog, and other species. 100% sequence conservancy and FIG. 17 | (1, 22) | 20 | TLR4; TLR2 | TLR4 (1); additional target(s) among proteins of TLR2 pathway |
| 4R9 | RQIKIWFQNRRMKWKK LRQQVELYRLLSR SEQ ID NO: 18 | Fourth helical region of TLR4 TIR (helix D) | FIG. 14 | ND | | h, m, rat, bovine, pig, and other species | (1) | 20 | TLR4 | ND[4] |
| 4R11/4αE | RQIKIWFQNRRMKWKK HIFWRRLKNALLD SEQ ID NO: 19 | Fifth helical region of TLR4 TIR (helix E) | FIG. 14 | ND | | h, m, rat, bovine, pig, and other species | (1) | 20 | TLR4 | TLR4 (1) |
| | | | | | | TLR2 BASED, TIR-DERIVED DECOY PEPTIDES | | | | |
| 2R1 | RQIKIWFQNRRMKWKK RKPKK APCRDVCYD SEQ ID NO: 20 | TLR2. Linker to the transmembrane region | FIG. 15 | ND | | m | — | 40 | TLR2 | ND |
| 2R3 | RQIKIWFQNRRMKWKK ENSDPPFKLC SEQ ID NO: 21 | AB loop and a part of strand B. | FIG. 15A, 15B, 16C | ND | | m | — | 40 | TLR2 | ND |
| 2R9 | RQIKIWFQNRRMKWKK PQRFCKLRKIMNT SEQ ID NO: 22 | Fourth helical region of TLR2 TIR (helix D) | FIG. 15A, 15B | ND | | h, m, bovine, dog, pig | — | 40 | TLR2 | ND |
| 2BB | RQIKIWFQNRRMKWKK LHKRDFVPGKWIID SEQ ID NO: 23 | BB loop of TLR2 TIR | FIG. 16A, 16B | ND | | h, m, rat, bovine, pig, and other | (22) | 40 | TLR2; TLR4 | Proteins of TLR2 and TLR4 pathways |
| 2DD-αD | RQIKIWFQNRRMKWKK EPIERKAIPQRFCK SEQ ID NO: 24 | DD loop and fourth helical region of TLR2 TIR (helix D) | FIG. 16 | ND | | m | — | 40 | TLR2 | ND Overlaps with 2R9 |

[1]Species specificity was determined based on interspecies sequence conservancy.
[2]Effective concentration depends on cell type and experimental conditions. The listed effective concentrations were determined for thioglycollate-elicited mouse macrophages. See references (1, 22, 30) for further details.
[3]Some peptides may have multiple targets and, therefore, affect the signaling through several mechanisms.
[4]underlined sequence is the antennapedia homeodomain translocating segment (SEQ ID NO: 50).
[5]not determined.

The TIR domain peptides that make up the TIR-derived decoy peptides (not fused to the Antennapedia homeodomain cell-permeating peptide or fused to other cell-permeating moiety) are also encompassed within the scope of the invention. These TIR domain peptides may be utilized in the same manner as the decoy peptides, where the assistance of a cell permeability factor is not required or is provided by other means. The present invention includes the TIR domain peptides set forth in Table 2.

TABLE 2

TIR domain peptides

| Peptide name | Sequence | SEQ ID NO: | Prototype protein - main structural element |
|---|---|---|---|
| TIRAP BASED, TIR DOMAIN PEPTIDES ||||
| TR3a | EGSQASLRCF | 25 | AB loop and a part of strand B |
| TR5a | ELCQALSRSHCR | 26 | Second helical region of TIRAP TIR (helix B) |
| TR6a | PGFLRDPWCKYQML | 27 | Third helical region of TIRAP TIR (helix C) |
| TR9a | AAYPPELRFMYYVD | 28 | Fourth helical region of TIRAP TIR (helix D) |
| TR11a | GGFYQVKEAVIHY | 29 | Fifth helical region of TIRAP TIR (helix E) |
| TRAM BASED, TIR DOMAIN PEPTIDES ||||
| TM4a | IVFAEMPCGRLHLQ | 30 | BB loop of TRAM TIR |
| TM4-ΔCa | IVFAEMPCG | 31 | Truncated BB loop of TRAM TIR |
| TM6a | ENFLRDTWCNFQFY | 32 | Third helical region of TRAM TIR (helix C) |
| TRIF BASED, TIR DOMAIN PEPTIDES ||||
| TF4a | CEEFQVPGRGELH | 33 | BB loop of TRIF TIR |
| TF5a | CLQDAIDHSGFT | 34 | Second helical region of TRIF TIR (helix B) |
| TF5-ΔCa | CLQDAIDHS | 35 | Second helical region of TRIF TIR (helix B) |
| MYD88 BASED, TIR DOMAIN PEPTIDES ||||
| M3a | EQTDYRLKLC | 36 | AB loop and a part of strand B. |
| M4a | SDRDVLPGTCVWS | 37 | BB loop |
| M5a | IASELIEKRCRRM | 38 | Second helical region of MyD88 TIR (helix B) |
| TLR4 BASED, TIR DOMAIN PEPTIDES ||||
| 4R1a | AGCKKYSRGESIYD | 39 | TLR4. Linker to transmembrane region |
| 4R3a | EEGVPRFHLC | 40 | AB loop and part of strand B. |
| 4R4/4BBa | LHYRDFIPGVAIAA | 41 | BB loop of TLR4 TIR |
| 4R9a | LRQQVELYRLLSR | 42 | Fourth helical region of TLR4 TIR (helix D) |
| 4R11/4αEa | HIFWRRLKNALLD | 43 | Fifth helical region of TLR4 TIR (helix E) |
| TLR2 BASED, TIR DOMAIN PEPTIDES ||||
| 2R1a | RKPKKAPCRDVCYD | 44 | TLR2. Linker to the transmembrane region |
| 2R3a | ENSDPPFKLC | 45 | AB loop and a part of strand B. |
| 2R9a | PQRFCKLRKIMNT | 46 | Fourth helical region of TLR2 TIR (helix D) |
| 2BBa | LHKRDFVPGKWIID | 47 | BB loop of TLR2 TIR |
| 2DD-αDa | EPIERKAIPQRFCK | 48 | DD loop and fourth helical region of TLR2 TIR (helix D) |

The variants of the present invention are based on the TIR-derived decoy peptides and the TIR domain peptides provided herein. The variants have similar or the same activity as the decoy peptides and the domain peptides, where the variants have one or two amino acid changes, individually selected from additions, substitutions and deletions, based on the amino acid sequence of the unaltered version of the peptide. The one or two changes may be limited to the portion of the peptide corresponding to a TIR domain, or the portion of the peptide corresponding to the cell-permeating peptide, or both. When amino acid substitutions are made, the substitutions may be conservative or non-conservative substitutions. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Mutations can also be introduced randomly along all or part of a peptide of the invention, such as by saturation mutagenesis, and the resultant variants can be screened for the activity.

The TIR-derived decoy peptides and the TIR domain peptides, and the variants thereof, of the present invention may be used in a number of different applications, primarily related to blocking or inhibiting TLR signaling. Because TLR signaling requires interaction between two TIR domain-containing proteins, such as dimerization of two or more TLRs, recruitment of TIR domain-containing adapter proteins to activated TLRs, and interaction of two or more TIR domain-containing adapter proteins, interruption of TIR::TIR interactions can block or inhibit many different aspects of TLR signaling pathways. Therefore, the present invention includes methods of inhibiting TIR:TIR interaction between two TIR domain-bearing proteins comprising contacting a cell expressing TIR domain-bearing proteins with an effective amount of one or more of the TIR-derived decoy peptides and the TIR domain peptides, or variants thereof, of the present invention. In a particular aspect, the invention is drawn to methods of inhibiting TIR:TIR interaction between two TIR domain-bearing proteins comprising contacting a cell expressing TIR domain-bearing proteins with an effective amount of one or more of the TIR-derived decoy peptides, or variants thereof.

The TIR domain-bearing proteins are TLRs, or TLR adapter proteins, or both. The TLRs may be any TLR, for example, but not limited, one or more receptors selected from the group consisting of TLR1, TLR2, TLR3, TLR4, TLR5, TLR6, TLR7, TLR8, TLR9, TLR10, TLR11, TLR12, and TLR13. In a one aspect, the TLR is TLR2 or TLR4, or both. The TLR adapter protein may be any TLR adapter protein, for example, but not limited to, one or more proteins selected from the group consisting of TIRAP, MyD88, TRIF, and TRAM. The one or more TIR-derived decoy peptides are those provided in Table 1. The one or more TIR domain peptides are those provided in Table 2. In one example, the TIR-derived decoy peptides are one or more selected from the group consisting of TR3, TR5, TR6, TR9 and TR11.

The invention is also includes methods of inhibiting TLR activation comprising contacting a cell expressing TLRs with an effective amount of one or more of the TIR-derived decoy peptides and the TIR domain peptides, or variants thereof, of the present invention. In a particular aspect, the invention is drawn to methods of inhibiting TLR activation comprising contacting a cell expressing TLRs with an effective amount of one or more of the TIR-derived decoy peptides, or variants thereof.

The TLRs may be any TLR, for example, but not limited, one or more receptors selected from the group consisting of TLR1, TLR2, TLR3, TLR4, TLR5, TLR6, TLR7, TLR8, TLR9, TLR10, TLR11, TLR12, and TLR13. In a one aspect, the TLR is TLR2 or TLR4, or both. The one or more TIR-derived decoy peptides are those provided in Table 1. The one or more TIR domain peptides are those provided in Table 2. In one example, the TIR-derived decoy peptides are one or more selected from the group consisting of TR3, TR5, TR6, TR9 and TR11.

The invention further includes methods of inhibiting TLR-mediated signaling comprising contacting a cell expressing TLRs with an effective amount of one or more of the TIR-derived decoy peptides and the TIR domain peptides, or variants thereof, of the present invention. In a particular aspect, the invention is drawn to methods of inhibiting TLR-mediated signaling comprising contacting a cell expressing TLRs with an effective amount of one or more of the TIR-derived decoy peptides, or variants thereof.

The TLRs may be any TLR, for example, but not limited, one or more receptors selected from the group consisting of TLR1, TLR2, TLR3, TLR4, TLR5, TLR6, TLR7, TLR8, TLR9, TLR10, TLR11, TLR12, and TLR13. In a one aspect, the TLR is TLR2 or TLR4, or both. The one or more TIR-derived decoy peptides are those provided in Table 1. The one or more TIR domain peptides are those provided in Table 2. In one example, the TIR-derived decoy peptides are one or more selected from the group consisting of TR3, TR5, TR6, TR9 and TR11.

In each of these aspects of the invention, the cell contacted with the peptide(s) in vitro, such as in a laboratory experiment, including a screening assay; in vivo, such as in a method of treating a disease or condition in a subject, or even ex vivo.

The effective amount of decoy peptides, domain peptides and variants thereof used in the in vitro methods described herein will vary depending on a cell type and experimental conditions when the cell is contacted. However, in general, an effective amount is between about 0.5 and 100 uM, and includes between about 0.5 and 100 uM, between about 1 and 75 uM, between about 5 and 50 uM, between about 20 and 40 uM and about 0.5 uM, 1 uM, 5 uM, 10 uM, 15 uM, 20 uM, 25 uM, 30 uM, 35 uM, 40 uM, 45 uM, 50 uM, 55 uM, and 60 uM.

A preparation comprising one or more of the decoy peptides, domain peptides and variants thereof may be prepared by adding the peptides to PBS (phosphate-buffered saline) or cell culture medium.

The TIR-derived decoy peptides and the TIR domain peptides, and the variants thereof, of the present invention may also be used in methods of treating diseases and conditions in subjects suffering from or afflicted with a condition exacerbated by TLR signaling. For example, the invention is drawn to methods of treating a subject having a condition mediated by TLR signaling comprising administering to a subject in need thereof a therapeutically-effective amount of a pharmaceutical composition comprising one or more of the TIR-derived decoy peptides and the TIR domain peptides, and variants thereof, of the present invention and a pharmaceutically acceptable carrier or diluent. In a particular aspect, the invention is drawn to methods of treating a subject having a condition mediated by TLR signaling comprising administering to a subject in need thereof a therapeutically-effective amount of a pharmaceutical composition comprising one or more of the TIR-derived decoy peptides, and variants thereof, and a pharmaceutically acceptable carrier or diluent. The one or more TIR-derived decoy peptides are those provided in Table 1. The one or more TIR domain peptides are those provided in Table 2. In one example, the TIR-derived decoy peptides are one or more selected from the group consisting of TR3, TR5, TR6, TR9 and TR11.

The condition mediated by TLR signaling may be any condition where disregulation of a TLR signaling pathway results in a disease or condition in a subject that might be cured, improved, lessened, etc. by inhibiting or blocking TLR signaling in the subject. Such conditions include, but are not limited to, inflammation, septic shock, or an inflammatory or genetic disease promoted by excessive TLR activation which exacerbates or causes the disease. In a specific example, the condition is septic shock. Thus, the invention is also drawn to methods of treating a subject having septic shock or other inflammatory condition comprising administering to a subject in need thereof a therapeutically-effective amount of a pharmaceutical composition comprising one or more of the TIR-derived decoy peptides and the TIR domain peptides, and variants thereof, of the present invention and a pharmaceutically acceptable carrier or diluent. In a particular aspect, the invention is drawn to methods of treating a subject having septic shock or other inflammatory condition comprising administering to a subject in need thereof a therapeutically-effective amount of a pharmaceutical composition comprising one or more of the TIR-derived decoy peptides, and variants thereof, and a pharmaceutically acceptable carrier or diluent. The one or more TIR-derived decoy peptides are those provided in Table 1. The one or more TIR domain peptides are those provided in Table 2. In one example, the TIR-derived decoy peptides are one or more selected from the group consisting of TR3, TR5, TR6, TR9 and TR11.

The peptides of the present invention can be formulated in a pharmaceutical composition that is suitable for administration to a subject. The pharmaceutical compositions comprise one or more the peptides and optionally a pharmaceutically acceptable diluent, carrier, and/or excipient, such as a sterile water for injection, PBS, buffer, a surfactant, a dispersing agent, a preservative, a solubilizing agent, and isotonicity agent, or any other pharmacologically inert vehicle for delivering the peptides of the invention to a subject. Conventional techniques for preparing pharmaceutical compositions are disclosed, for example in: Remington, The Science and Practice of Pharmacy, 19th ed., Gennaro, Ed., Mack Publishing Co., Easton, Pa. 1995.

The pharmaceutical compositions of the present invention may be formulated, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of pharmaceutical formulations can be used to effect such administration.

Depending on the means of administration, the dosage may be administered all at once, such as with an oral formulation in a capsule or liquid, or slowly over a period of time, such as with an intramuscular or intravenous administration.

The therapeutically-effective amount of peptide will vary depending upon the physical characteristics of the subject, the severity of the subject's symptoms, the particular disease or condition being treated, the formulation and the means used to administer the peptides, the number of doses being administered to the subject over the course of treatment, and the method being practiced. The specific dose for a given subject is usually set by the judgment of the attending physician. However, it is considered that the effective amount of decoy peptides, domain peptides and variants thereof used in the methods of treatment described herein will generally be between about 0.1 nmol/g and 50 nmol/g, and includes between about 1 nmol/g and 50 nmol/g, between about 1 nmol/g and 30 nmol/g, between about 5 nmol/g and 40 nmol/g, and between about 5 nmol/g and 25 nmol/g. Suitable values also include about 0.5 nmol/g, 2 nmol/g, 4 nmol/g, 6 nmol/g, 8 nmol/g, 10 nmol/g, 12 nmol/g, 14 nmol/g, 16 nmol/g, 18 nmol/g, 20 nmol/g, 22 nmol/g, 24 nmol/g, and 26 nmol/g.

Administration frequencies for the pharmaceutical compositions of the present invention include 4, 3, 2 or once daily, every other day, every third day, every fourth day, every fifth day, every sixth day, once weekly, every eight days, every nine days, every ten days, bi-weekly, monthly and bi-monthly. The duration of treatment will be based on the condition being treated and will be best determined by the attending physician. However, continuation of treatment is contemplated to last for a number of days, weeks, or months.

In each of these embodiments, the subject is a human, a non-human primate, bird, horse, cow, goat, sheep, a companion animal, such as a dog, cat or rodent, or other mammal.

III. Examples

TIRAP Based, TIR-Derived Decoy Peptides

Materials and Methods
Animals and Cell Culture

C57BL/6J mice were obtained from The Jackson Laboratory (Bar Harbor, Me.). Primary peritoneal macrophages were obtained by peritoneal lavage 4 days after intraperitoneal injection (3 ml) of sterile 3% thioglycolate broth. Washed cells were resuspended in RPMI 1640 which contained 2% FBS, 1% penicillin:streptomycin and 2 mM L-glutamine. After plating, cells were incubated overnight at 37° C. and then washed with PBS to remove non-adherent cells. Cells were exposed to peptides 30 min before stimulation with a TLR agonist.

Design and Synthesis of Peptides

Eleven TIR-derived decoy peptides representing the surface of the TIRAP TIR domain, as well as a control peptide (CP; RQIKIWFQNRRMKWKKSLHGRGDPMEAFII; SEQ ID NO:49) (19) comprising a random amino acid sequence, were synthesized jointly with the cell-permeating *Drosophila* Antennapedia homeodomain sequence (RQIKIWFQNRRMKWKK; SEQ ID NO:50). The set of TIRAP TIR-derived decoy peptides was designed so that each peptide represents a non-fragmented patch of TIRAP TIR surface, and the entire set encompasses the TIR surface. The decoy peptides were synthesized, purified and verified by the Biopolymer and Genomics Core Facility at the University of Maryland Baltimore. Peptides were synthesized on a Prelude peptide synthesizer (PTI Instruments, Boston, Mass.) using Fmoc coupling. Peptide stocks were diluted in 0-25% DMSO/$H_2O$ and quantified according to (20).

Isolation of mRNA and RT-PCR

Total cellular RNA was isolated using Tripure from Roche (San Francisco, Calif.) following manufacture's protocol. RNA was then reverse transcribed using AMV Reverse Transcriptase from Promega (Madison, Wis.) with poly-T priming as per manufacturer's directions. cDNA was then quantified by real-time PCR using Applied Biosystems Fast SYBR Green PCR Master Mix and an ABI Prism 7500HT cycler. Primers used for detection: hypoxanthine phosphoribosyltransferase (HPRT) (forward: GCTGACCTGCTGATTACATTAA (SEQ ID NO:51), reverse: TGATCATTACAGTAGCTCTTCAGTCTGA (SEQ ID NO:52)), TNFα (forward: GACCCTCACACTCAGATCATCTTCT (SEQ ID NO:53), reverse: CCACTTGGTGGTTTGCTACGA (SEQ ID NO:54)), IL-1β (forward: AAATACCTGTGGCCTTGGGC (SEQ ID NO:55), reverse: CTTGGGATCCACACTCTCCAG (SEQ ID NO:56)), IFNβ (forward: CACTTGAAGAGCTATTACTGGAGGG (SEQ ID NO:57), reverse: CTCGGACCACCATCCAGG (SEQ ID NO:58)) and RANTES (forward: CTGCTTTGCCTACCTCTCCCT (SEQ ID NO:59), reverse: GAGTGACAAACACGACTGCAAGAT (SEQ ID NO:60)). The primers were designed using Primer Express 2.0 (Applied Biosystems). Using HPRT as reference, the ΔCt method was used to calculate relative gene expression. One-way ANOVA was preformed, as well as Dunnett's multiple comparison post hoc test with a $p \le 0.01$ selected as the level of significance.

SDS-PAGE and Western Analysis

Cellular protein extracts were isolated by addition of 240 μL per well cold lysate buffer (20 mM Tris, 50 mM NaCl, 1.5 mM $MgCl_2$, 2 mM EDTA, 10 mM NaF, 2 Mm DTT, 1 mM $Na_3VO_4$, 1% Triton). Cells were incubated with lysis solution for 30 min on agitator at 4° C. Lysate was then collected and centrifuged at 14,000 g for 10 minutes at 4° C. After quantification using BioRad protein assay, protein samples were added to Laemmli buffer and then boiled for 10 min. Samples were then resolved by SDS-10% PAGE in Tris/glycine/SDS buffer (25 mM Tris, 250 mM glycine, 0.1% SDS), and transferred onto Immobilon P transfer membranes (Millipore, Bedford, Mass.) (100 V, 1.5 h, 4° C.). Membranes were blocked for 1 h in TBS-T (20 mM Tris-HCl, 150 mM NaCl, 0.1% Tween 20) containing 5% nonfat milk, then probed for overnight at 4° C. with the respective antibodies (Abs) (dilution 1:1000 in TBS-T with 2% BSA). After washing in TBS-T, membranes were incubated with secondary HRP-conjugated, donkey anti-rabbit IgG (1:10,000 dilution in TBS-T with 5% nonfat milk) for 1 h at room temperature. Membranes washed five times in TBS-T before development with ECL reagents (GE Healthcare) according to manufacturer's directions.

Cytokine Detection

Cytokine secretion was measured in supernatant samples collected at 6 or 24 h time points and stored at −80° C. Samples were analyzed by a multiplex assay at the University of Maryland Baltimore Cytokine Core Facility using a Luminex 100 reader and Softmax Pro software, or by ELISA kits for mouse IL-6 or TNF-α from BioLegend (San Diego, Calif.) and LT-4000 microplate reader.

Reagents

Protein-free *Escherichia coli* K235 LPS was used at final concentration of 10 ng/ml to stimulate cells. S-[2,3-bis(palmitoyloxy)-(2-RS)-propyl]-N-palmitoyl-(R)-Cys-Ser-Lys$_4$-OH (P3C) and S-[2,3-bis(palmitoyloxy)-(2-RS)-propyl][R]Cys-Ser-Lys$_4$-OH (P2C) were purchased from EMC microcollections GmbH (Tubingen, Germany) and used for cell stimulation at 500 and 50 ng/ml, respectively. Phospho-ERK1/2 and phospho-JNK1/2 rabbit Abs were obtained from Cell Signaling Technology, Inc. β-actin rabbit Ab were from SantaCruz Biotechnology, Inc.

Results

Design of TIRAP TIR-Derived Decoy Peptides. TIRAP Peptides Inhibit LPS-Induced Cytokine mRNA Expression TIRAP/Mal functions to facilitate MyD88 recruitment to the activated TLR4 and TLR2, presumably through a simultaneous interaction with receptor and MyD88 TIR domains. Therefore, multiple TIR:TIR interaction sites are expected in TIRAP TIR. The decoy peptide approach was used to obtain leads on the functional protein-protein interfaces within TIRAP/Mal, a TLR adapter protein. To this end, eleven TIRAP TIR-derived decoy peptides were designed to be structurally homologous to the TLR4 TIR-derived decoy peptides used previously (1), so that each peptide represents a non-fragmented patch of the TIRAP TIR surface, with the entire domain encompassed by the set of peptides. The TIRAP TIR-derived decoy peptides were synthesized in tandem with the cell-permeating sequence of Antennapedia homeodomain (21) and each peptide was tested for the ability to inhibit TLR4 and TLR2 signaling in primary mouse macrophages. Peptide sequences and the structural regions they represent are shown in reference (30).

The effects of TRAP TIR-derived decoy peptides on LPS-induced cytokine mRNA expression were examined. The 1 h cytokine expression was measured in the initial peptide screening because previous work suggested that the early cytokine mRNA expression provides the most direct and unbiased readout for overall evaluation of TLR inhibitory peptides (1, 19, 22). Five TRAP TIR-derived decoy peptides, TR3, TR5, TR6, TR9 and TR11, significantly inhibited the IFNβ and Rantes cytokine mRNA production at 5 µM concentration, as well as moderately inhibited the IL-1β mRNA production (FIG. 1A). At a 20 µM concentration, these five decoy peptides exerted a stronger inhibition of the IL-1β, IFNβ, and RANTES mRNA and were also able to inhibit potently TNFα expression (FIG. 1B).

When used at a high concentration, the peptide derived from the BB loop of TIRAP, TBB (TR4), inhibited the cytokine induction to some extent, although the inhibition was weaker than the effects of peptides derived from the neighboring TIRAP regions, TR3 and TR5 (FIG. 1B). TNFα mRNA was least affected by TBB compared to the other cytokine mRNAs examined (FIG. 1B). These findings are in full agreement with previously published observations that TBB is the least potent inhibitor among the decoy peptides derived from the BB loops of four TLR adapters (19) and IFNβ induction is inhibited by this peptide (23).

Two additional peptides were examined for the ability to inhibit LPS-induced TNFα mRNA. Peptide TR45 comprised the C-terminal portion of TBB and the N-terminal part of the TR5 decoy (30), so that the decoy part of TR45 is centered on the border region represented by TBB and TR5. Such a modification did not enhance the inhibitory ability of the modified peptide over TBB or TR5 (FIG. 1C). The second modified peptide tested was TR9-sh, which includes only the central portion of TR9 (Table 1). Deletion of both ends of TR9 markedly diminished the inhibition exerted by this peptide (FIG. 1C), thus suggesting that one or both ends of TR9 are important for full inhibitory activity of this peptide.

TRAP TIR-Derived Decoy Peptides Inhibit LPS-Induced MAPK Activation

Figure 2:
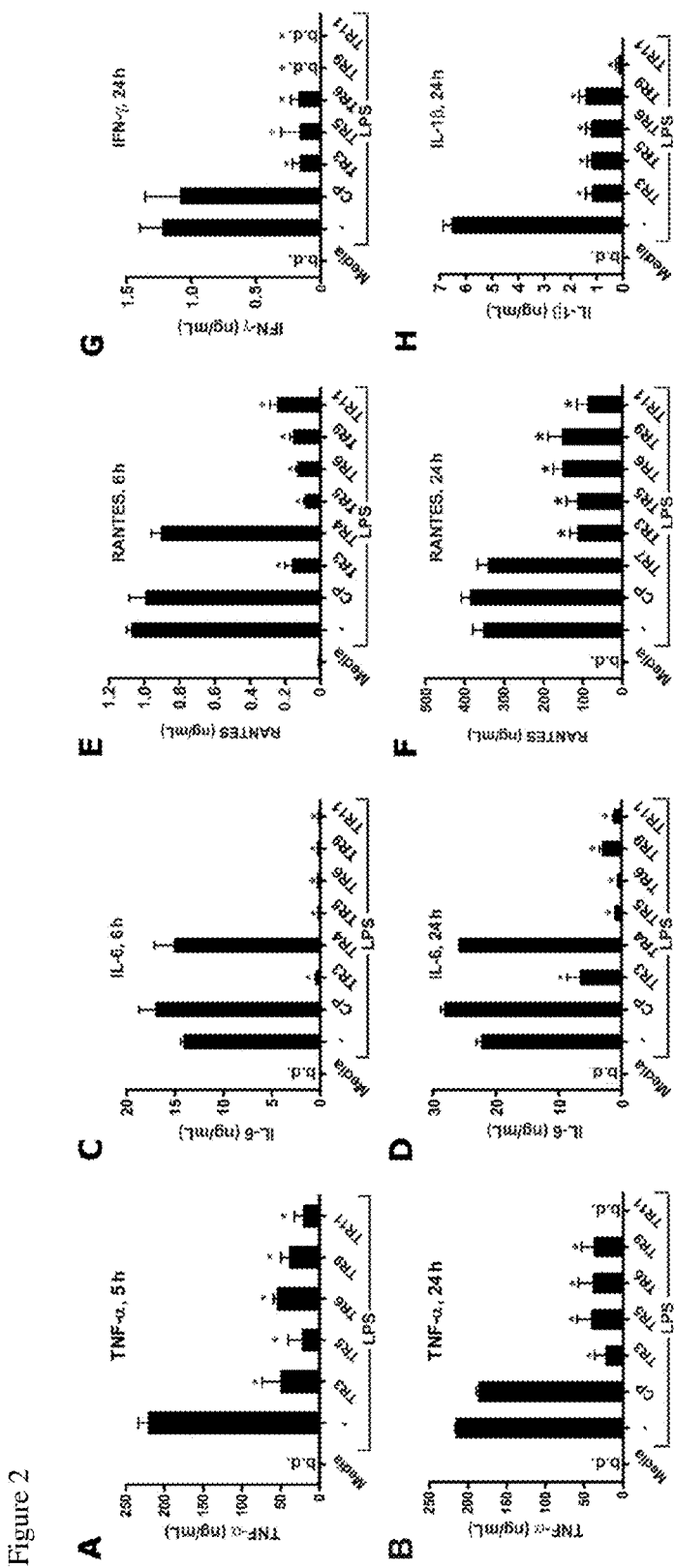
FIG. 2. Inhibition of LPS-induced cytokine secretion by cell-permeable decoy peptides derived from TIRAP TIR. Primary macrophages were stimulated with LPS (10 ng/ml) for 5 (FIG. 2A), 6 (FIG. 2C and FIG. 2E), or 24 h (FIG. 2B, FIG. 2D, FIG. 2F-2H). Peptide treatments were carried out as described in FIG. 1. Data show mean and SEM for 3 separate experiments. Decrease in cytokine production induced by TR3, TR5, TR6, TR9 and TR11 is statistically significant ($p<0.05$) in all 8 panels.

The five TIRAP TIR-derived decoy peptides that were able to inhibit LPS-induced cytokine mRNA expression, TR3, TR5, TR6, TR9, and TR11, also potently inhibited ERK phosphorylation induced by a 30 min LPS stimulation (FIG. 1D). TR7, TR8, and TR10 also diminished ERK activation, although their effect was weaker (FIG. 1D and not shown). Neither TIRAP peptide activated ERK in cells incubated without a TLR agonist (not shown). JNK, however, was moderately activated in macrophages after 1 hour incubation in the presence of 20 µM of TR3, TR6, or TR7 (not shown). This activation resulted in the apparent absence of JNK inhibition by TR3 and TR6 peptides (FIG. 1D). Previously, it was reported that the cell-permeable decoy peptide derived from the BB loop of TLR2 induces the JNK and p38 MAPK phosphorylation, but does not activate ERK (22). The mechanism of this differential MAPK activation by select peptides, although interesting, is not understood at this time. Peptides TR9 and TR11 inhibited both ERK and JNK MAPKs (FIG. 1D). Peptide-induced inhibition of ERK persisted over a long period of time. FIG. 1E demonstrates that TR6 and TR11 prevent the LPS-induced ERK activation for duration of at least 1 hour post-stimulation Inhibition of TLR4-Mediated Cytokine Production by TIRAP TIR-Derived Decoy Peptides To evaluate further the translational potential of peptide TLR inhibitors, the effects of inhibitory TIRAP TIR-derived decoy peptides on LPS-induced IL-6 production were studied. Inhibition of cytokines by decoy peptides was confirmed at the protein level. All five inhibitory TIRAP peptides abolished the LPS-induced IL-6 production measured in 6 h supernatants (FIG. 2C). The IL-6 production remained profoundly suppressed throughout 24 h incubation after a single dose treatment of macrophages with an inhibitory peptide (FIG. 2D). Peptides TR3, TR5, TR6, TR9, or TR11, but not CP or TBB, also inhibited the Rantes production measured in 6 h supernatants (data not shown). The IL-6 secretion was strongly induced by LPS, as IL-6 concentration continued to grow during overnight incubation, thereby indicating the prolonged secretion of this cytokine by LPS-stimulated macrophages (FIG. 2). Ability of decoy peptides to inhibit the IL-6 secretion over a long period after a single dose treatment implies the high translational potential of these substances as TLR inhibitors or lead therapeutics.

Effects of TIRAP TIR-Derived Decoy Peptides on TLR2 Signaling

TIRAP/Mal was first identified as an adapter that facilitates the agonist-dependent recruitment of MyD88 to TLR4 (14, 15). TIRAP/Mal is also implicated in TLR2 signaling, because a knockout of TIRAP gene affects both TLR4- and TLR2-mediated cellular responses (17, 24). A more recent study has specified further that, rather than playing an obligatory role in TLR2 signaling, TIRAP sensitizes TLR2 signaling, as Mal-deficient macrophages are still capable to respond to high doses of TLR2 agonists, although the response is diminished (25).

Figure 3:
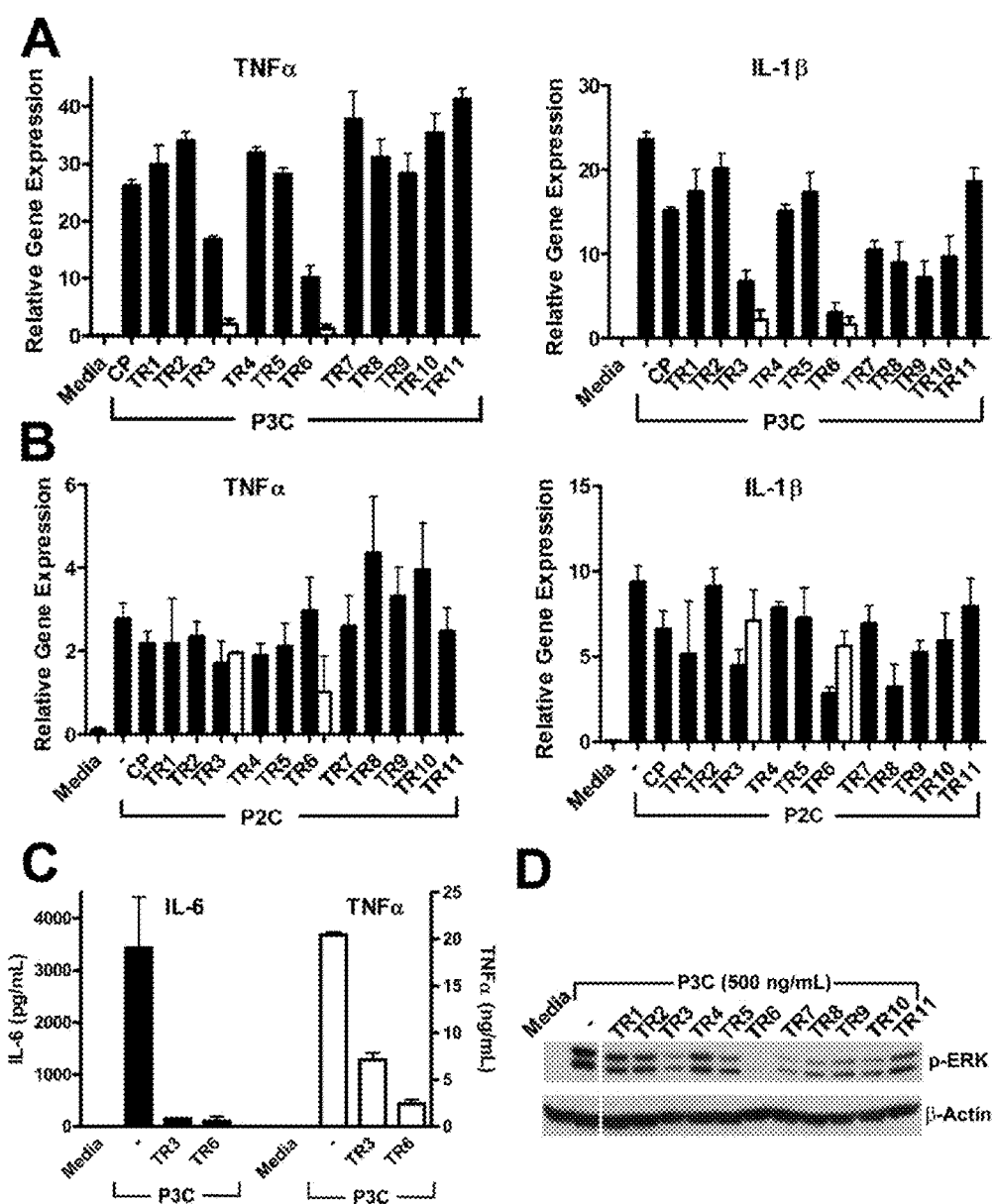
FIG. 3. Effect of TIRAP decoy peptides on TLR2 signaling. Thioglycollate-elicited macrophages were incubated in the presence of 20 (black columns) or 40 µM (open columns) of a decoy peptide for 30 min prior to stimulation with P3C (500 ng/ml) (FIG. 3A and FIG. 3C) or P2C (50 ng/ml) (FIG. 3B). Cytokine mRNA expression was measured 1 h after TLR2 stimulation and is normalized to the expression of HPRT gene.

Because of the role TRAP plays in TLR2 signaling, TIRAP TIR-derived decoy peptide effects on TLR2-induced cytokine mRNA expression were examined. Thioglycollate-elicited mouse macrophages were stimulated either by P2C, an agonist that induces signaling through TLR2/TLR6 heterodimerization, or P3C, a TLR2/TLR1 agonist, and effects of TIRAP TR-derived decoy peptides on induction of cytokine mRNA were examined. At 5 µM concentration, the TIRAP peptides did not affect P2C- or P3C-induced TNFα and IL-1β mRNA (data not shown). At the 20 µM concentration, TR3 and TR6 inhibited the TNFα and IL-1β mRNA induced by P3C (FIG. 3A); however, effect of these peptides on the P2C-induced cytokines was significantly less (FIG. 3B). Peptides that showed the moderate inhibition of TLR2 signaling at 20 µM, TR3 and TR6, were examined at higher concentration. Both TR3 and TR6 profoundly inhibited the P3C-induced TNFα and IL-1β mRNA at the 40 µM concentration (FIG. 3A). In sharp contrast to the P3C-activated induction, these peptides did not affect significantly the P2C-induced TNFα and IL-1β mRNA even at this higher dose (FIG. 3B). To confirm the inhibitory effect of TR3 and TR6 on P3C-induced signaling, IL-6 and TNF-α concentration was measured in macrophage supernatants collected 5 h after stimulation of cells with P3C. Secretion of both cytokines was profoundly inhibited after treatment of cell with TR3 or TR6 (FIG. 3C). Concordantly, both TR3 and TR6 diminished the P3C-induced ERK phosphorylation (FIG. 3D).

Discussion

Figure 18:
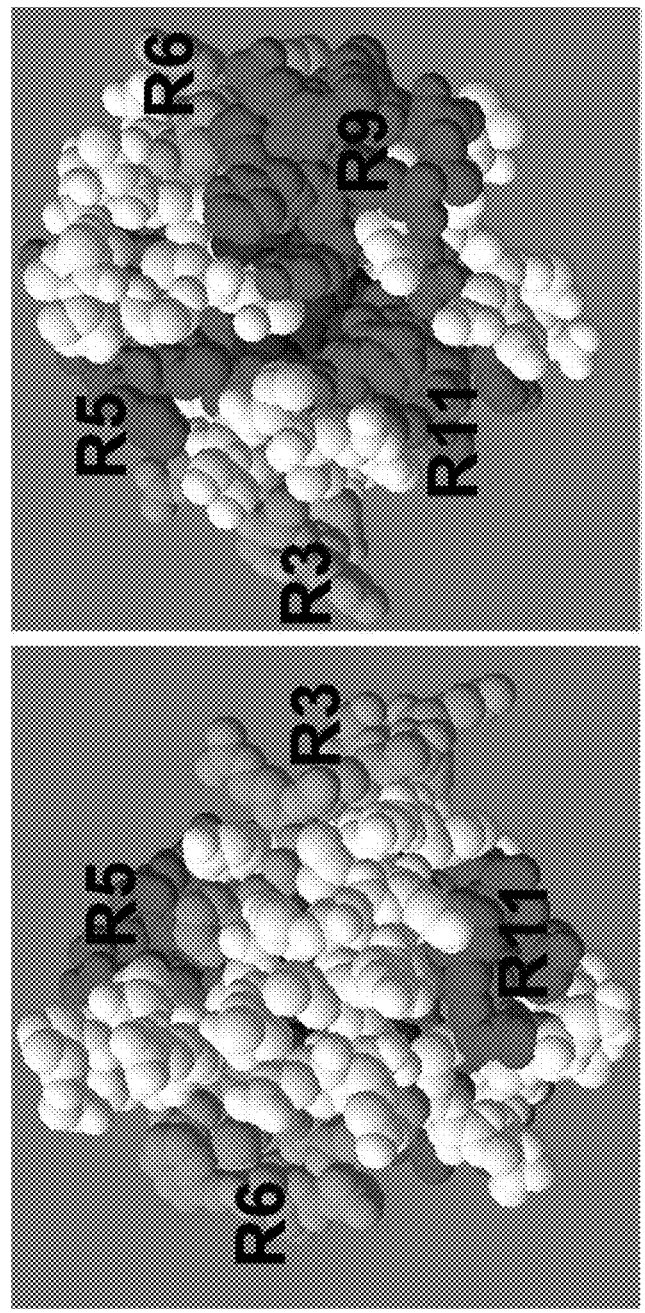
FIG. 18. Relative positions of inhibitory peptides on the TIRAP TIR surface. Regions represented by peptides that potently inhibit TLR4 signaling are shown in red. Peptides that inhibit both TLR4 and TLR2 signaling are shown blue.

The TIRAP TIR-derived decoy peptides tested in this work were designed so that each peptide represents a region that is structurally homologous to the corresponding TLR4 TIR region (1, 30). Five TIRAP TIR-derived decoy peptides, TR3, TR5, TR6, TR9 and TR11, potently inhibited TLR4 signaling. This set is different from the set of inhibitory peptides derived from the TLR4 TIR, in which peptides from regions 1, 3, 4 (BB loop), 9, and 11 were inhibitory. Peptides derived from regions 3, 9, and 11 of both TLR4 and TIRAP TIRs are inhibitory. Noteworthy, the sequences of these TIRAP and TLR4 regions are very dissimilar (Table 1 and reference (1)); for example, the inhibitory peptides derived from regions 3 of TRAP and TLR4 TIRs have sequences EGSQASLRCF (SEQ ID NO:25) and EEGVPRFHLC (SEQ ID NO:40), correspondingly. The absence of local sequence conservancy, especially in the surface-exposed segments of TIR domains, is well documented (e.g., (26)). Decoy peptides derived from regions 5 and 6 of TIRAP/Mal potently inhibit LPS signaling, while decoy peptides from the structurally homologous regions of TLR4 are poor inhibitors. Regions 5 and 6 represent surface exposed amino acids that are adjacent to the C strand, the most central strand of TIR β-sheet that spans the core of the domain. Therefore, regions 5 and 6 are not contiguous on the TIR surface (FIG. 18) and unlikely to represent one TIRAP interface. Instead of decoy peptide derived from TRAP region 5, decoy peptide derived from the BB loop of TLR4, a neighboring region to region 5, inhibited LPS signaling. The BB loop of TLR4 and several other TIR domains are involved in TIR homo-dimerization (1, 27, 28). Poor inhibitory activity of TRAP BB decoy peptide may indicate that the TIRAP/Mal homo-dimerization may not be important for function of this protein. Although TIRAP/Mal is necessary for recruitment of MyD88, and not TRIF, to the TLR4 signaling complex, all inhibitory TIRAP decoy peptides blocked both MyD88-dependent and MyD88-independent cytokine genes. This finding agrees with and expands previous reports that TIR-derived peptides do not affect preferentially the MyD88-dependent cytokine production (1, 19, 22). Ability of TIRAP TIR-derived decoy peptides to inhibit both MyD88-dependent and MyD88-independent cytokines suggests that TLR4 recruits adapters of MyD88-dependent or MyD88-independent pathways either through same or significantly overlapping sites.

Two TRAP TIR-derived decoy peptides, TR3 and TR6, inhibited TLR2/TLR1-mediated signaling. Interestingly, TR3 and TR6 inhibited P3C-, but not P2C-induced signaling. This finding might suggest that these peptides target TLR1. However, regions 3 and 6 are located on opposite sides of TRAP TIR (FIG. 18); therefore, it is unlikely that they target same molecule. Further studies are required to understand molecular mechanisms that underlay specificity and strength of TLR inhibition by TIR decoy peptides. TR3 represents the AB loop of TIRAP/Mal. The highly surface-exposed residues of this loop include two charged amino acids, E128 and R135, and a polar amino acid Q131. Interestingly, the same motif (-ExxQxxxR-) formed by E152, Q155, and R159 is also present in TR5 (Table 1 and 2). Because these TIRAP regions have different secondary structure and, therefore, the residues are spaced differently on the TIRAP surface, it is unlikely that these regions would have the same docking sites. Nevertheless, the corresponding peptides have higher conformational flexibility and may be predicted to target the same binding site. Counterargument for the statement that the -ExxQxxxR- sequence is solely responsible for inhibition by both TR3 and TR5, is that the TR45 peptide, which is not a strong inhibitor of TLR4 (FIG. 1C), also has this motif. In addition to TLR4, TR3 inhibits TLR2 signaling, while TR5 does not. This finding suggests that the -ExxQxxxR- motif does not play a major role in binding of TR3 to TLR2.

New data confirm previous findings that the peptide derived from BB loop of TRAP, TR4 (QLRDAAPGGAIVS; SEQ ID NO:61), is not a particularly strong inhibitor of TLR4 (19). Interestingly, peptide derived from same region of TLR4 TIR (4BB) (LHYRDFIPGVAIAA (SEQ ID NO:41) (the underlined are residues identical in structurally homologous TLR4 and TRAP peptides)), is a quite potent inhibitor of TLR4 that targets TLR4 TIR dimerization surface (1, 22). Comparison of TR4 and 4BB sequences suggests that hydrophobic amino acids of 4BB at positions 6, 7 and 10 might be important for binding of 4BB to its target.

Region 6 represents the N-terminal part of the third helical region of TIRAP TR. Decoy peptide derived from region 6 of TIRAP, TR6 (PGFLRDPWCKYQML; SEQ ID NO:27), inhibited both TLR4 and TLR2 signaling; whereas decoy peptides derived from the structurally homologous region of TLR4 (RHFIQSRWCIFEYE; SEQ ID NO:62) did not inhibit TLR4 quite as strongly. Sequence conservancy between TR6 and the homologous TLR4 region is less than that in the BB loop region, and it is yet to be determined which residues of TR6 are more important for the inhibitory properties of this peptide.

Decoy peptides derived from region 9 (the extended fourth helical region) and region 11 (the fifth TIR helix) of both TRAP and TLR4 TIR inhibit the LPS signaling. Yet, there is very little sequence similarity in the corresponding regions of TIRAP and TLR4. TR9 represents the region that has been identified as the TRAF6 binding site (29). Further studies are required to elucidate if TR9 indeed targets TRAF6.

IV. Examples

TRAM Based, TIR-Derived Decoy Peptides

Materials and Methods
Animals, Cell Culture and Treatment

C57BL/6J mice were obtained from The Jackson Laboratory (BarHarbor, Me.). Harvesting, culturing, and stimulation of peritoneal macrophages were described in previous publications (1, 18, 19). *Escherichia coli* K235 LPS (34) was used at the final concentration of 100 ng/ml. The 2,3-bis(palmitoyloxy)-(2-RS)-propyl-N-palmitoyl-(R)-Cys-Ser-Lys$_4$-OH (P3C) and S-[2,3-bis(palmitoyloxy)-(2-RS)-propyl]-[R]Cys-Ser-Lys$_4$-OH (P2C) (EMC Microcollections, Tubingen, Germany) were used at 500 and 50 ng/ml, respectively. Oligonucleotide (ODN) 1668 and low m.w. polyinosinic-polycytidylic acid [poly(I:C)] in complex with LyoVec were obtained from InvivoGen; these agonists were used at 2.5 µM and 400 ng/ml, respectively.

Peptide Synthesis and Reconstitution

Peptides were obtained through the Biopolymer and Genomics Core Facility (University of Maryland, Baltimore, Md.). All lyophilized peptides were of >95% purity. Peptide stocks were quantified by spectrophotometry (20) after reconstitution and stored at −80° C. Peptide sequences are shown in Table 3.

TABLE 3

Sequences of TRAM peptides

| Peptide Name | Peptide Sequence | Structural Region | SEQ ID NO: |
|---|---|---|---|
| TM1 | GAGAEEQDEEEFLK | segment preceding βA[a] | 63 |
| TM2 | AEDDTDEALRVQDL | AA and αA | 64 |
| TM3 | QNDFGIRPG | αA, AB, and BB | 65 |
| TM4[b] | IVFAEMPCGRLHLQ | BB and αB | 30 |
| TM4-N | IVFAE | BB | 66 |
| TM4-M | EMPCG | BB | 67 |
| TM4-C | RLHLQ | αB | 68 |
| TM4-ΔN | MPCGRLHLQ | BB and αB | 31 |
| TM4-ΔM | IVFARLHLQ | BB and αB | 69 |
| TM4-ΔC | IVFAEMPCG | BB | 70 |
| TM4-E/A | IVFAAMPCGRLHLQ | BB and αB | 71 |
| TM4-P/H | IVFAEMHCGRLHLQ | BB and αB | 72 |
| TM4-C/H | IVFAEMPHGRLHLQ | BB and αB | 73 |
| TM5 | NLDDAVNGSAWT | αB and BC | 74 |
| TM6 | ENFLRDTWCNFQFY | αC and CD | 32 |
| TM7 | TSLMNSVSRQHKYNS | CD | 75 |
| TM8 | RPLNSPLPRE | βD and DD | 76 |
| TM8/9 | PRERTPLALQTINA | DD and βE | 77 |
| TM9 | RTPLALQTINA | DD and βE | 78 |
| TM9/10 | QTINALEEES | βE and EE | 79 |
| TM10 | LEEESQGFSTQVE | βE, EE, and αE | 80 |
| TM11 | RIFRESVFERQQS | αE | 81 |
| CP | SLHGRGDPMEAFII | Randomized sequence | 82 | a - Structural regions of TIR domain are designated as follows: helices are designated by Greek α, for example, αA, helix A; strands are indicated by Greek β; loops are indicated by two capital letters, for example, AA, loop that connects strand A and helix A.
b - This peptide was previously described as TRAM-BP (19).

Expression Vectors

The full-length murine TRAM or TRIF TIR N-terminally tagged with hemagglutinin (HA) or Flag tag was cloned into the pEF-BOS vector. TLR4-Cer expression vector was described earlier (1).

Cytokine ELISA

A total of 2×10$^6$ cells was plated in 12-well plates and treated with peptides for 30 min prior to LPS stimulation. TNF-α, IL-1β, IL-6, and IFN-β were measured using ELISA kits from BioLegend (San Diego, Calif.), as recommended by the manufacturer.

Immunoblotting and Coimmunoprecipitation

HEK293T cells were transfected with indicated plasmids using Superfect Transfection Reagent (Qiagen). Twenty-four hours posttransfection, the cells were lysed using the buffer containing 20 mM HEPES (pH 7.4), 150 mM NaCl, 10 mM NaF, 2 mM Na$_3$VO$_4$, 1 mM EDTA, 1 mM EGTA, 0.5% Triton X-100, 0.1 M DTT, 1 mM PMSF, and protease inhibitor mixture (Roche, Indianapolis, Ind.). Rabbit Ab against phospho-ERK, phospho-JNK, MyD88 (D80F5), STAT1-Y701, total STAT1, and GAPDH were purchased from Cell Signaling Technology (Beverly, Mass.). Rabbit anti-phospho-p38 Ab was purchased from Promega (Madison, Wis.). Goat anti-TLR4 (M-16), rabbit anti-TLR4 (H-80), anti-HA-HRP (F-7), and rabbit anti-b-actin Ab were purchased from Santa Cruz Biotechnology. Mouse anti-Flag M2 and rabbit anti-HA Ab were from Sigma-Aldrich. GFP Ab (A1122) was from Invitrogen. Protein was quantified using Bio-Rad protein quantification kit. Equal amount of protein was loaded and analyzed by 10% SDS-PAGE and immunoblotting. The cell extracts containing equal amount of protein were incubated with 1 µg Ab for 2 h, followed by 4-h incubation with 25 µl protein G agarose beads (Roche); the beads were then washed four times with lysis buffer, boiled in 13 sample loading buffer, and analyzed by immunoblotting.

Quantitative Real-Time RT-PCR

Total RNA was isolated with Nucleospin RNA II kits (Macherey-Nagel, Bethlehem, Pa.), followed by DNase digestion. cDNA was synthesized from 1 µg RNA using Goscript transcriptase (Promega), and subjected to real-time PCR with gene-specific primers for HPRT, TNF-α, IL-1β, IFNβ, and RANTES on H7900 ABI system using Fast SYBR Green master mix (Applied Biosystems, Foster City, Calif.).

Cell Viability Analysis

A total of 5×10$^4$ mouse peritoneal macrophages was plated into 96-well tissue culture plates, incubated overnight, and treated with peptides for 3 h. After the treatment, cells were incubated with MTT at 0.5 mg/ml (Sigma-Aldrich) for 3 h. Fifty microliters DMSO was added to cells before reading OD at 540 nm.

TRAM TIR Model

The model was visualized and analyzed using DeepView/Swiss-pdbViewer (Swiss Institute of Bioinformatics).

Animal Experiments

Eight-week-old C57BL/6J mice were injected with 1 or 17.5 µg/g animal weight of *E. coli* K235LPS i.p. Peptides reconstituted in PBS were administered i.p. or i.v. Control groups received equivalent volume of solvent (PBS). The blood samples were collected 1, 2, 4, and 8 h, or 2, 8, and 24 h after LPS challenge. The plasma samples were obtained and kept frozen until TNF-α and IL-6 were measured by ELISA. Survival of animals was monitored every 6-16 h after LPS challenge. All animal experiments were carried out with institutional approval.

Results
Identification of Inhibitory Peptides

TRAM TIR decoy peptides were designed similarly to the TIRAP-derived peptides described above. Each TRAM peptide represents a structural element(s) that comprises a non-fragmented patch of TIR surface with all peptides collectively encompassing the TIR domain. The sequences of all TRAM-derived decoy peptides and the corresponding structural regions are provided in Table 3. The cell-permeating 16-aalong sequence of Antennapedia homeodomain (RQIKIW-FQNRRMKWKK; SEQ ID NO:50) (21) was placed at the N terminus of each decoy sequence to render peptides cell permeable. Two additional peptides, TM8/9 and TM9/10, that represent the border area between regions 8 and 9, and 9 and 10, respectively, were additionally tested.

To evaluate peptide-inhibitory activities, we first measured LPS-induced cytokine mRNA expression. Murine macrophages were pretreated with peptides (5 or 20 µM) for 30 min, and then the cells were stimulated with LPS (100 ng/ml) for 1 h. Two peptides, TM4 and TM6, potently inhibited the TLR4-mediated cytokine mRNA transcription (FIG. 5A, 5B). Decoy peptide TM4 is derived from the BB loop of TRAM TIR; we previously identified this peptide as an effective TLR4 inhibitor (19). TM4, even at the low dose of 5 µM, significantly decreased mRNA expression of all cytokines examined (FIG. 5A). Another TRAM-derived peptide that strongly inhibited mRNA transcription is TM6. TM6 effectively blocked induction of IFN-β and RANTES, two TRIF-dependent genes, at both concentrations used (FIG. 5A). However, the effect of TM6 at 5 µM on the MyD88-dependent cytokines, IL-1β and TNF-α, was not statistically significant. Both TM4 and TM6 potently inhibited expression of all cytokine genes at 20 µM (FIG. 5A).

To determine the duration of the inhibitory effect preliminary, we measured cytokine expression after 5-h incubation. Two cytokines, RANTES and IL-6, have been selected for this test because these cytokines are strongly expressed at this time point, whereas expression of TNF-α and IFN-β is more transient and significantly decreased 5 h post-stimulation (data not shown). Pretreatment of cells with 20 µM TM4 or TM6, but not with other peptides, profoundly suppressed expression of both cytokines, even at this late time point (FIG. 5B).

We next examined whether TRAM peptides inhibit the TLR4-mediated p38, ERK, and JNK MAPK activation. Murine macrophages pretreated with peptides for 30 min were challenged with LPS. Cell lysates were collected 30 min post-stimulation and analyzed for MAPK phosphorylation by Western analysis. Consistent with peptide effects on steady-state mRNA, both TM4 and TM6 inhibited activation of all three MAPKs (FIG. 5C). The inhibition of MAPKs by TM4 or TM6 was long lasting; it persisted for at least 1 h after LPS stimulation (data not shown). To characterize further the effects of TRAM peptides on MAPKs, murine macrophages were treated with TRAM peptides, but not challenged by LPS. Without LPS stimulation, TM3 weakly activated p38 and ERK MAPK, whereas effect of other peptides was insignificant compared with the LPS-induced activation (data not shown).

We previously demonstrated that LPS stimulation leads to STAT-1-Y701 phosphorylation through autocrine activation of type I IFN receptor by IFN-β (23). FIG. 5D confirms this observation and shows that both TM4 and TM6 block LPS-induced STAT-1-Y701 phosphorylation. Inhibition of STAT1 phosphorylation is a consequence of the strong effect of both peptides on IFN-β transcription (FIG. 5A).

Figure 6:
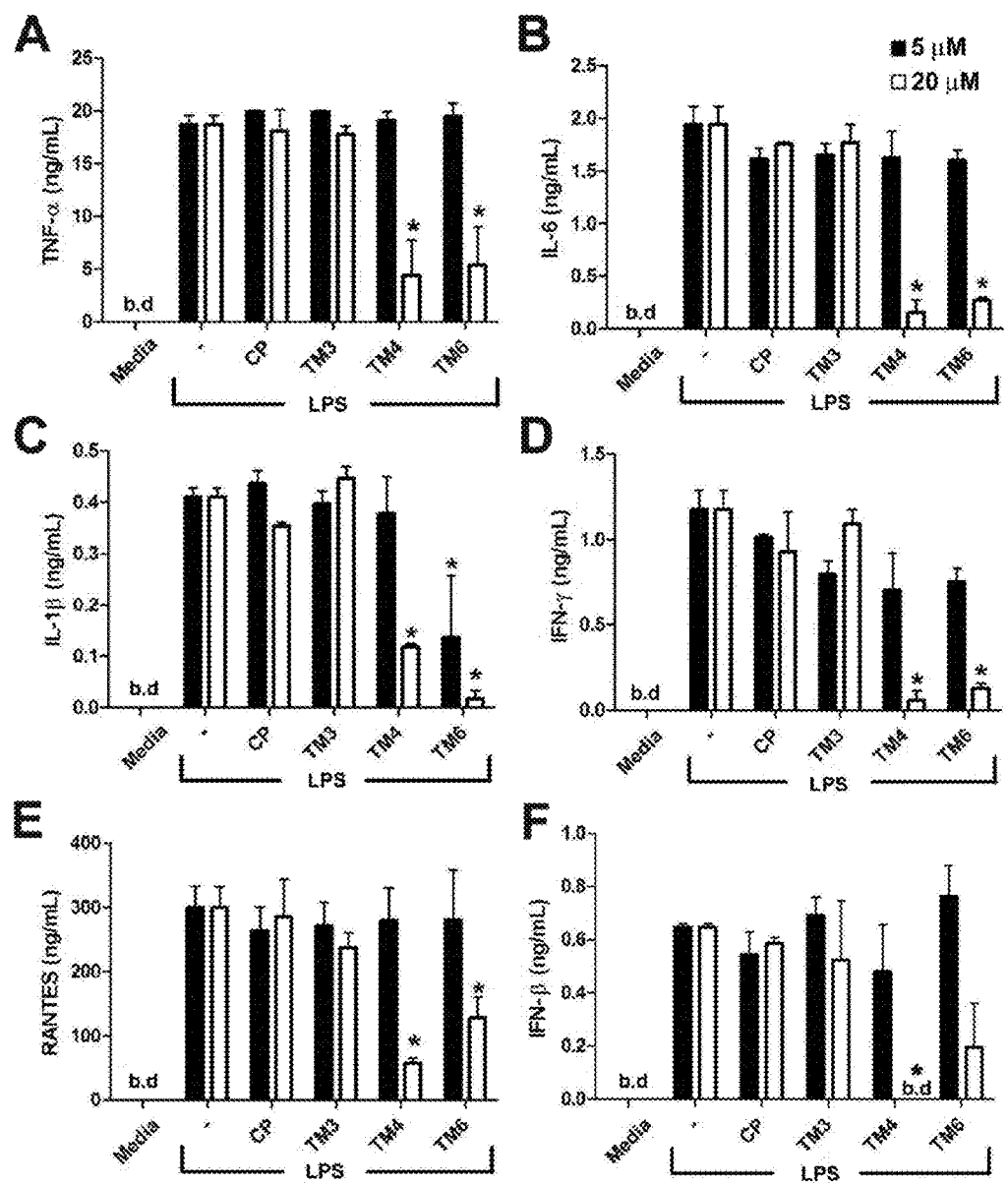
FIGS. 6. TM4 and TM6 inhibit LPS-induced cytokine secretion. Peritoneal macrophages were incubated in the presence of 5 or 20 µM of indicated TRAM peptides for 30 min prior to stimulation with LPS (100 ng/ml). Supernatants were collected 24 h later and analyzed for TNF-α (FIG. 6A), IL-6 (FIG. 6B), IL-1β (FIG. 6C), IFN-γ (FIG. 6D), RANTES (FIG. 6E) and IFN-β (FIG. 6F) contents. Data represent the means±s.e.m. of 3 independent experiments. *$p<0.01$. b.d. —below detection limit.

We next measured the effect of peptides on TNF-α, IL-6, IL-1β, IFN-γ, RANTES, and IFN-β secretion. Macrophage supernatants were collected 24 h after LPS stimulation, and cytokine contents were measured by ELISA. FIG. 6 shows that both TM4 and TM6 exert a strong and lasting inhibitory effect on secretion of all six cytokines examined (FIG. 6).

TM8, TM9, and TM10 peptides are derived from consecutive segments of TRAM primary sequence and represent adjacent areas on the TRAM TIR surface. To exclude the possibility of missing an inhibitory sequence due to arbitrary fragmentation of a peptide, we designed two additional peptides, TM8/9 and TM9/10, that overlap with TM8 and TM9, and TM9 and TM10, respectively (Table 3). Neither TM8/9 nor TM9/10 inhibited the TLR4 signaling significantly (data not shown).

Figure 7:
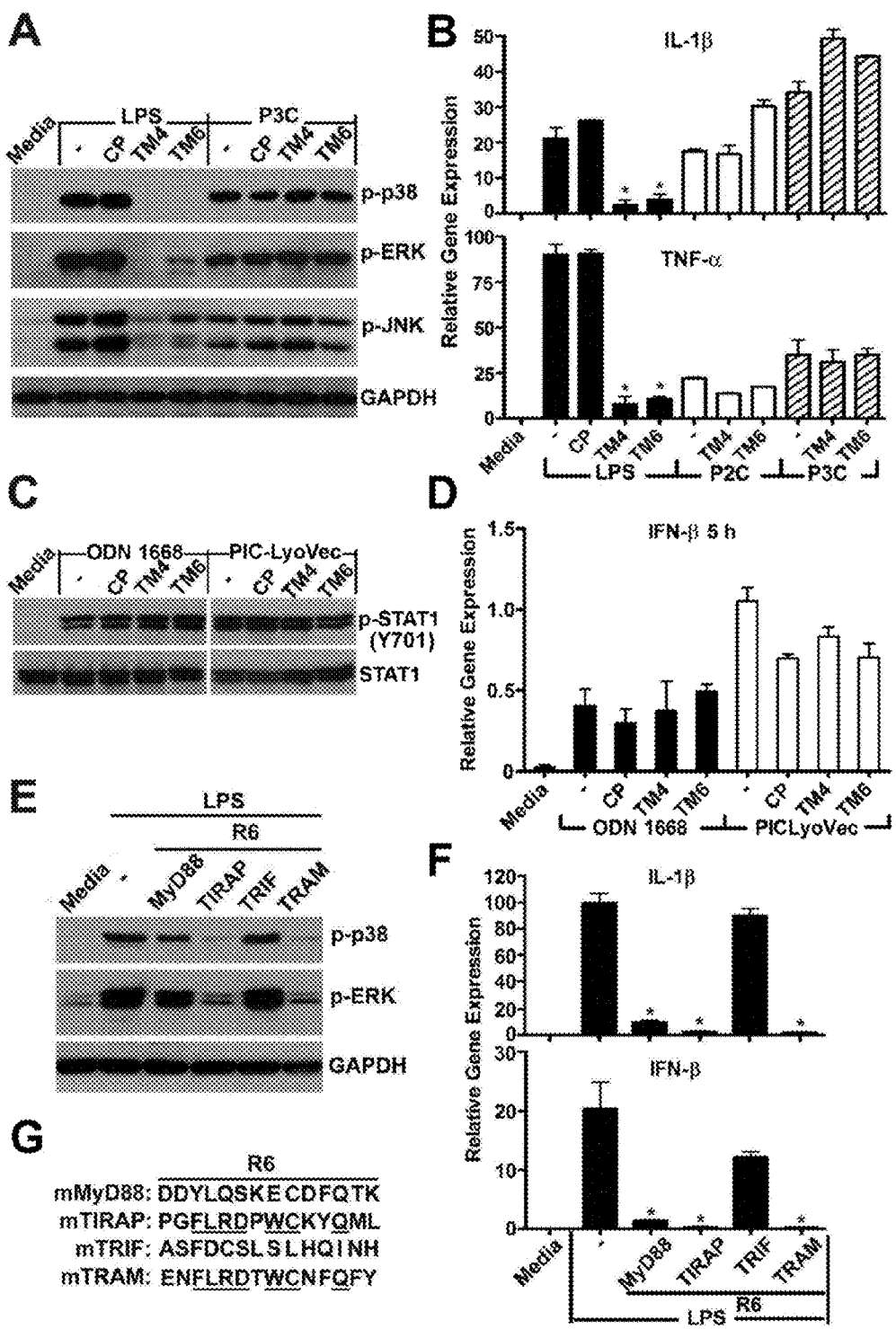
FIG. 7. TM4 and TM6 block TLR4, but not TLR2 (FIG. 7A, FIG. 7B), TLR9, or RIG-I-like receptor (FIG. 7C, FIG. 7D) signaling. Peptides derived from region 6 of TRAM and TIRAP TIR are strong inhibitors of TLR4-induced MAPK activation and cytokine transcription (FIG. 7E, FIG. 7F). Peptides were used at 20 µM. P2C and P3C were used at 50 and 500 ng/ml, respectively. Macrophages were treated with ODN 1668 at 2.5 µM or low m.w. poly(I:C) in complex with LyoVec at 400 ng/ml. MAPK phosphorylation was measured in whole-cell lysates collected 30 min after stimulation with LPS or P3C (FIG. 7A). To measure STAT1-Y701 phosphorylation, cells were stimulated with ODN 1668 for 5 h or with poly(I:C) in complex with LyoVec for 16 h (FIG. 7C). IFN-β mRNA induction by TLR9 and RIG-I-like receptor agonists was measured 5 h after stimulation (FIG. 7D). Other experimental details are as in FIG. 1. Data in (FIG. 7A) and (FIG. 7E) represent three independent experiments. Means 6 SEM of three independent experiments are shown in (FIG. 7B), (FIG. 7D), and (FIG. 7F). *$p<0.01$.
Figure 8:
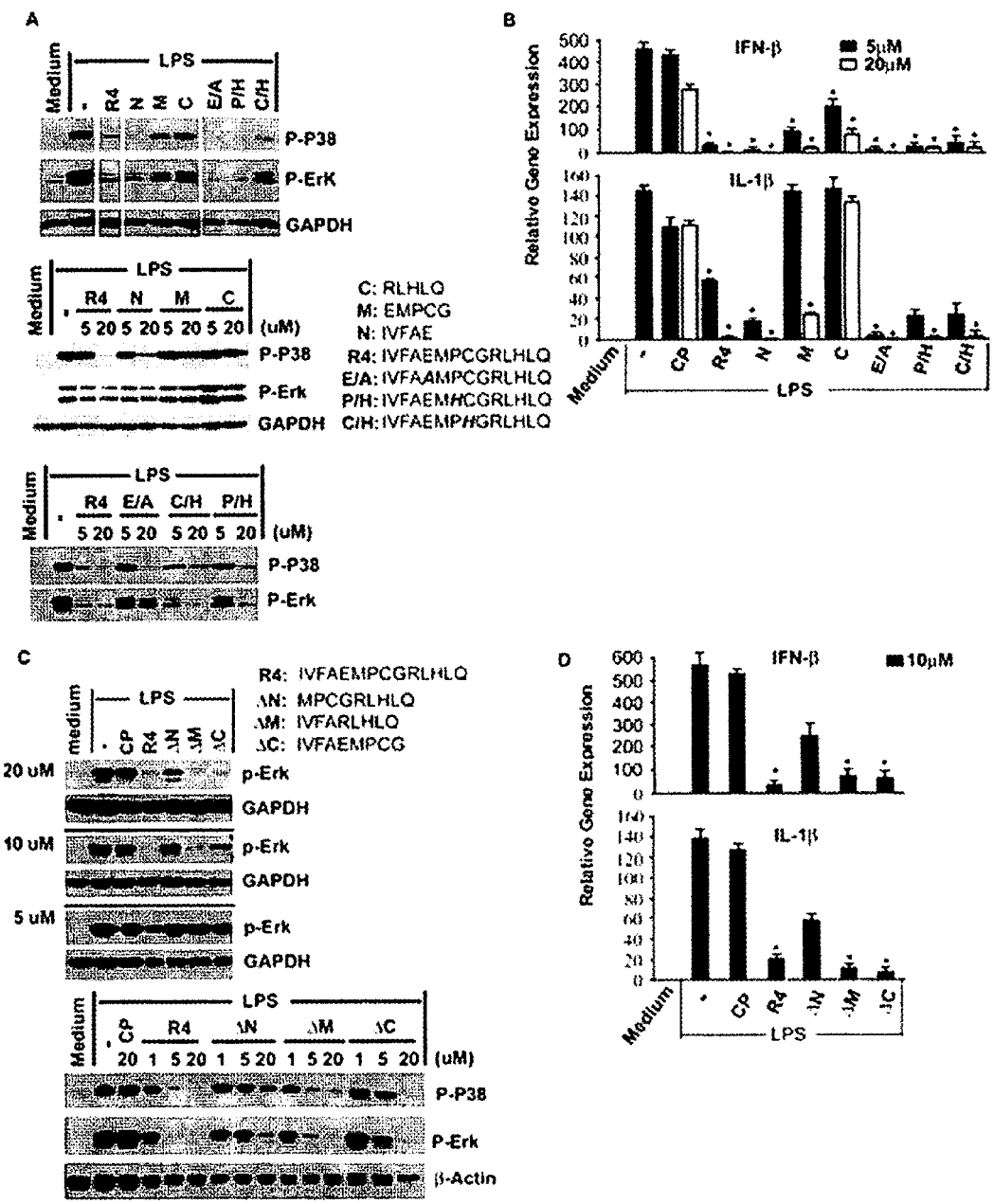
FIG. 8. Deletion analysis of TM4 peptide.

TRAM is an adapter protein selectively involved in TLR4 signaling (5, 9). We next studied whether the effects of TM4 and TM6 are specific and examined peptide effects on TLR2, TLR9, and retinoic acid-inducible gene 1 (RIG-I)/MDA-5 pathway. Mouse macrophages were stimulated with 500 ng/ml P3C or 50 ng/ml P2C, agonists that activate signaling through TLR2/TLR1 or TLR2/TLR6 heterodimers, respectively. In sharp contrast with the effect of these two decoy peptides on TLR4 signaling, TM4 and TM6 (20 µM) did not inhibit P3C- or P2C-induced p38, ERK, or JNK MAPK phosphorylation (FIG. 7A), or IL-1β and TNF-α mRNA induction (FIG. 7B). Neither peptide blocked cell activation induced by TLR9 or RIG-I/MDA-5 agonists, CpG oligonucleotide ODN 1668, or intracellularly delivered poly(I:C). The STAT1 Y701 residue was phosphorylated in macrophages in response to both agonists regardless of the presence of TRAM peptides, albeit the STAT1 activation by poly(I:C) occurred at later time points (FIG. 7C). TRAM peptides did not affect the induction of IFN-β mRNA by these agonists statistically significantly (FIG. 7D).

Peptide effects on cell viability were evaluated using the MTT test. Neither inhibitory peptide affected cell viability in a significant way, even after 3-h incubation in the presence of TM4 or TM6 (data not shown).

Figure 5:
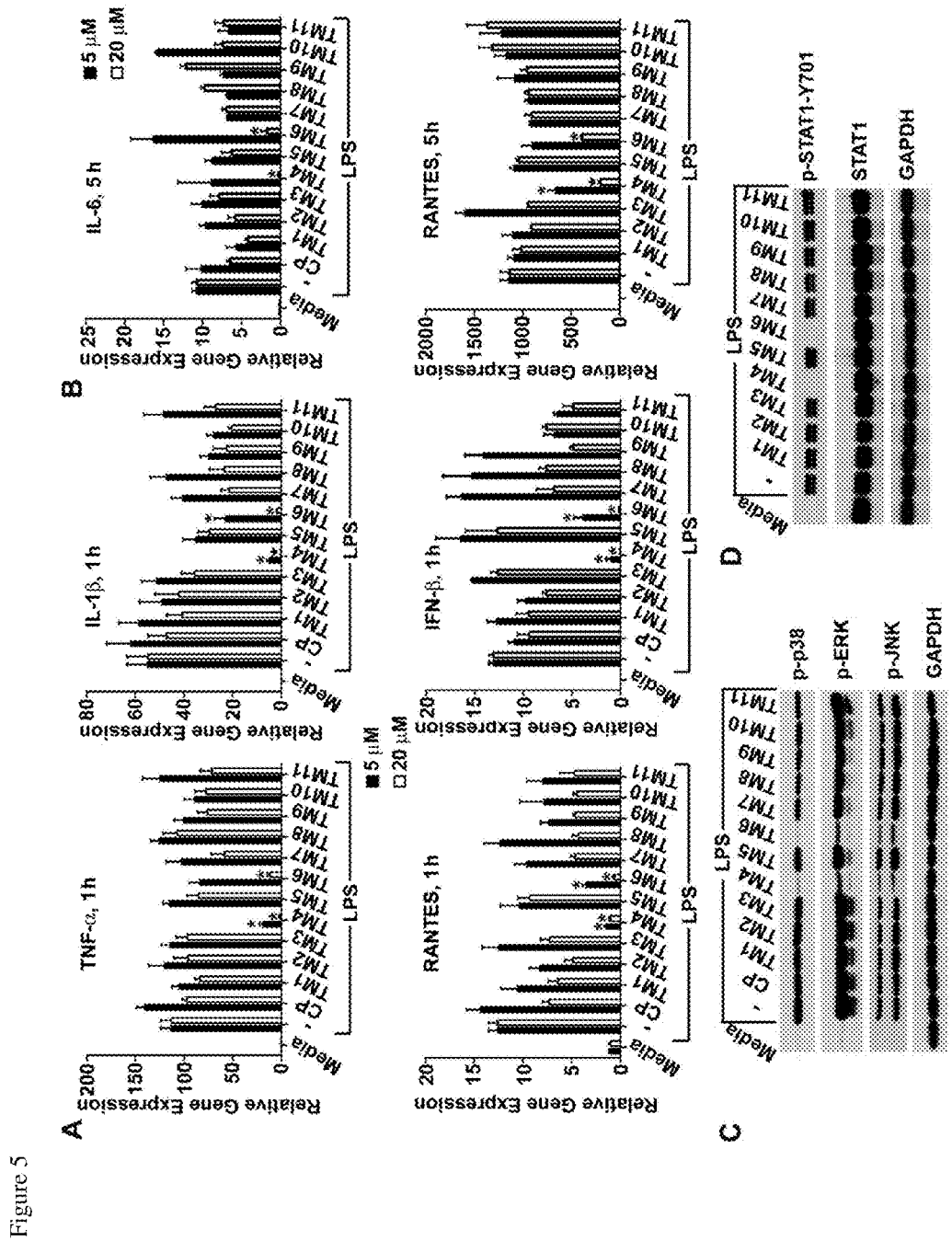
FIG. 5. TRAM decoy peptides derived from BB loop and third helical region, TM4 and TM6, inhibit LPS-induced cytokine mRNA and activation of MAPKs and STAT1.

Inhibitory Activities of Peptides Derived from the Third Helical Region of TLR Adapters We observed previously that peptides derived from the BB loop of TLRs and TLR adapters differ markedly in ability to inhibit TLR4 (19, 22). Our new data show that, in addition to the TRAM BB loop peptide, peptide derived from the third helical region of TRAM, TM6, strongly inhibits TLR4 signaling (FIGS. 5, 6). Interestingly, the sequence of the region represented by TM6 is highly similar to the sequence of the structurally homologous region of TIRAP/Mal (30) (FIG. 7G). TIRAP/Mal peptide derived from this region, TR6, inhibited both TLR4 and TLR2 signaling (30). We next compared inhibitory efficiency of peptides derived from the homologous structural region of other TLR4 adapters. Both TRAM and TIRAP region 6 peptides, TM6 and TR6, potently inhibited the LPS-induced activation of p38 and ERK MAPKs (FIG. 7E). These peptides also blocked transcriptional activation of IL-1b and IFN-b genes (FIG. 7F). In contrast, the inhibitory effects of peptides derived from homologous region of TRIF and MyD88 TIR were less (FIG. 7E, 7F), especially on MAPK activation. Notably, region 6 in TRAM and TIRAP is the most similar region in these proteins. TIRAP and TRAM region 6 sequences are PGFLRDP WCKYQML (SEQ ID NO:27) and ENFLRDTWCNFQFY (SEQ ID NO:32), respectively, and have 7 identical aa (underlined). This is by margin the highest degree of local sequence conservancy that has been found in all four TLR4 adapters. Such a high degree of local conservancy of the surface-exposed residues strongly suggests that this region is functionally important. It is noteworthy that there is no notable similarity in the homologous regions of MyD88 and TRIF (FIG. 7G).

Inhibitory Properties of Truncated TM4 Variants

TM4 is a very efficient overall inhibitor of TLR4 (FIG. 5). We next sought to identify amino acids that are critical for the inhibitory effects of TM4. We used three groups of modified peptides to address this question. First, three short peptides each of which contained only 5 aa of TM4 were examined.

TM4-N contains 5 N-terminal aa of TM4; TM4-M contains the TM4 middle 5-aa section; and TM4-C contains the 5 C-terminal aa (sequences are shown in Table 3). The second group is comprised of three modified TM4 peptides that lack TM4-N, TM4-M, and TM4-C; these peptides are designated as TM4-ΔN, TM4-ΔM, and TM4-ΔC, respectively (Table 3). Finally, we tested three peptides, TM4-E/A, TM4-P/H, and TM4-C/H, in which a single amino acid has been replaced (sequences are shown in Table 3).

Among three short peptides, TM4-N was the strongest inhibitor. TM4-M demonstrated intermediate inhibition, whereas TM4-C was least active (FIG. 8A, 8B). Consistently with these data, TM4-ΔN, a peptide that lacks the N terminus of TM4, was least inhibitory, whereas deletion of the TM4 C terminus did not affect peptide-inhibitory potency significantly (FIG. 8C, 8D). The inhibitory efficiency of TM4-ΔC is close to that of TM4. TM-ΔM also retains some inhibitory properties.

All three single amino acid replacements affected TM4 properties weakly. TM4-E/A, TM4-P/H, and TM4-C/H inhibited TLR4-induced MAPK activation (FIG. 8A) and cytokine expression (FIG. 8B), although the inhibitory efficacy of TM4-C/H was less than that observed for other two modified peptides. Collectively, these data demonstrate that the 5 N-terminal aa of TM4 peptide together with its middle segment are more important for TLR4 inhibition.

TM4 and TM6 Block Adapter Recruitment to TLR4

Figure 9:
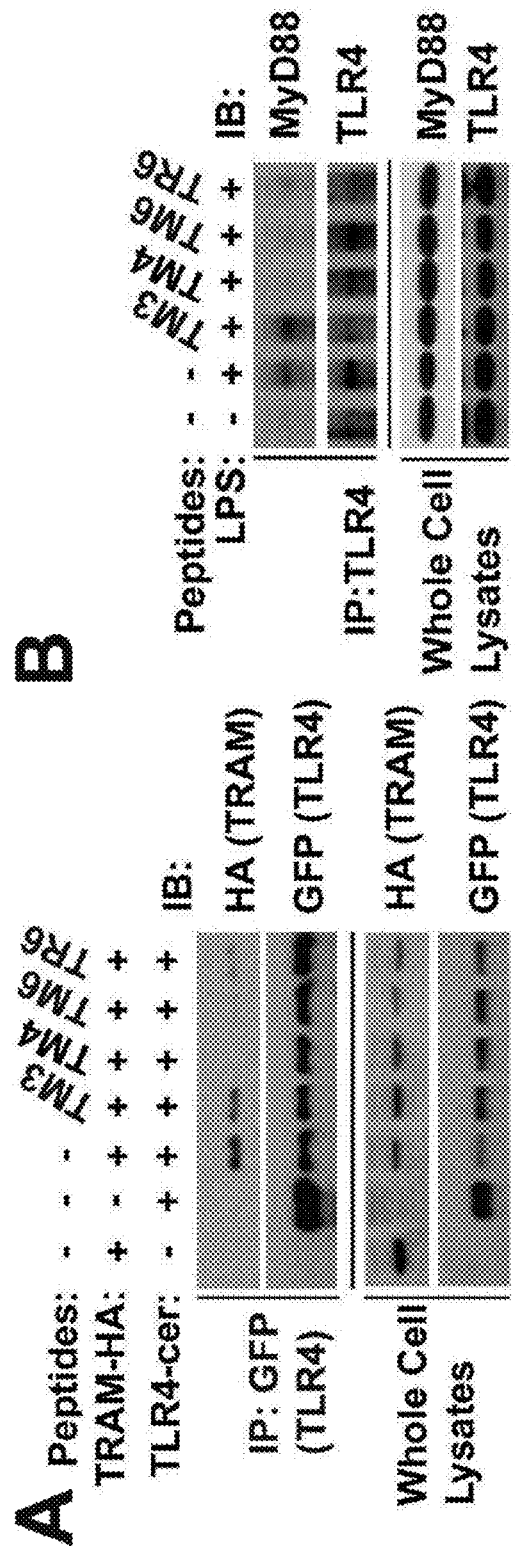
FIG. 9. TM4, TM6, and TR6 block adapter recruitment to TLR4.

We used coimmunoprecipitation assays to study peptide effects on TLR adapter recruitment. To study effect of peptides on TRAM recruitment, HEK293T cells were co-transfected with mouse TLR4 tagged with Cerulean fluorescent protein (TLR4-Cer) (1) and HA-tagged mouse TRAM (HA-TRAM). TM4 or TM6, but not a non-inhibitory TM3 peptide, blocked TLR4/TRAM coimmunoprecipitation (FIG. 9A). Interestingly, TR6, a TIRAP-derived inhibitory peptide that has a sequence similar to TM6, also inhibited TLR4/TRAM association, although less efficiently than TM6 (FIG. 9A).

To study peptide effects on MyD88 recruitment, we used primary mouse peritoneal macrophages. In this cellular model, MyD88 co-immunoprecipitates with TLR4 in the agonist-dependent manner (36) (FIG. 9B). All inhibitory peptides tested, TM4, TM6, and TR6, efficiently prevented the LPS-induced TLR4/MyD88 association (FIG. 9B). TIRAP/Mal is necessary for MyD88 recruitment to TLR4 (15), whereas TRAM recruits TRIF and is not required for MyD88 recruitment and activation of MyD88-dependent genes (33). Yet, TIRAP- and TRAM-derived peptides cross-reacted in the sense that each peptide blocked the recruitment of both adapters, TRAM and MyD88. This observation agrees fully with the fact that the adapter-derived peptides are equally effective inhibitors of MyD88- or TRIF-dependent cytokines (FIGS. 5, 6) (30). Collectively, these results suggest that TM4 and TM6 disrupt the assembly of TLR4 signaling complexes by blocking the TIR:TIR interactions required for adapter recruitment, possibly mediated by a common binding site for recruitment of TIRAP and TRAM to TLR4 TIR dimer.

Inhibitory Peptides Blunt LPS-Induced Cytokine Response in Mice

Figure 10:
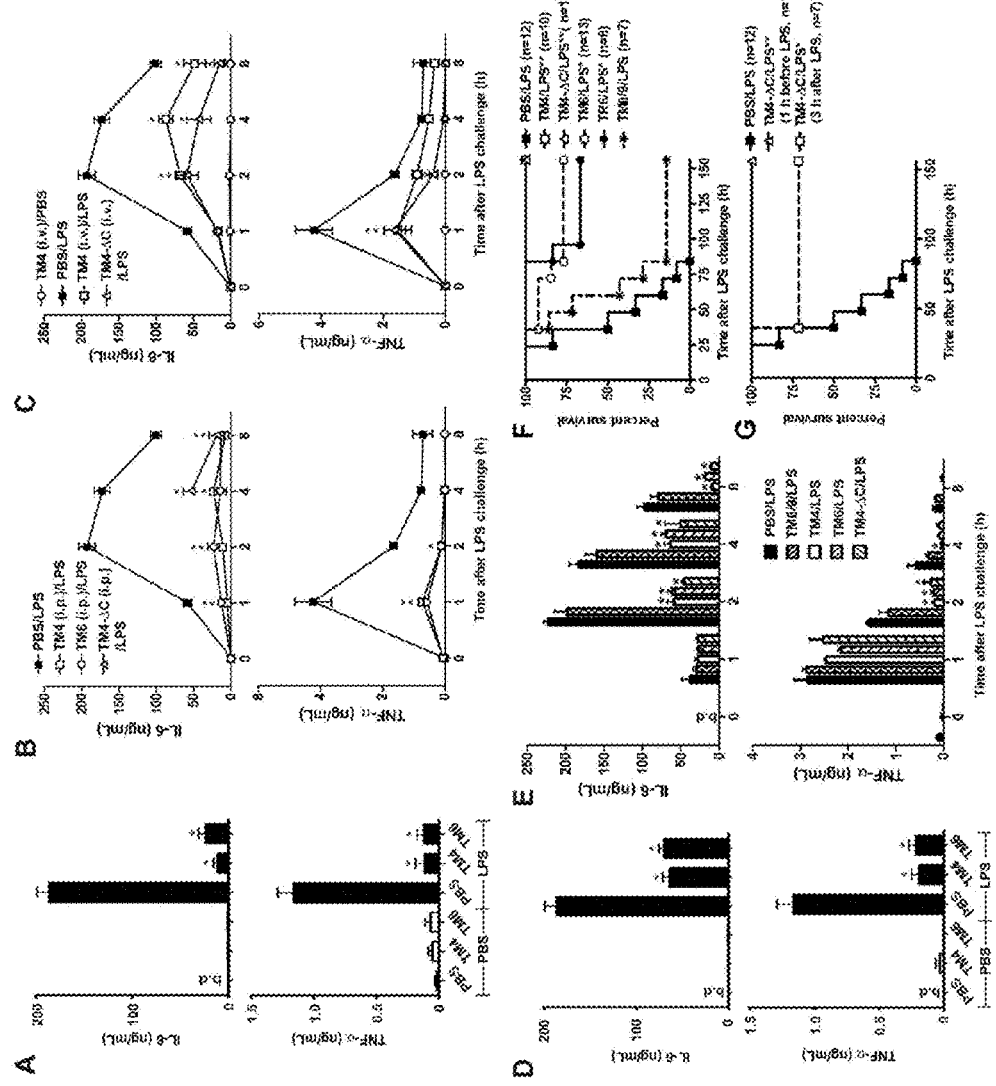
FIG. 10. TM4, TM6 and TM4-ΔC effectively suppress LPS-induced cytokine induction in vivo (FIGS. 10A-10E) and protect mice from lethal endotoxemia (FIG. 10F, FIG. 10G).

We next studied whether peptides identified as inhibitory in in vitro tests are effective in vivo. C57BL/6J mice were challenged i.p. with a sublethal LPS dose (1 µg/g animal weight), and plasma TNF-α and IL-6 levels were monitored for 8 h after the challenge. In the first series of experiments, we injected 10 nmol/g TM4 or TM6 i.p. 1 h before LPS challenge. The 10 nmol/g dose corresponds to 38, 41, and 32 mg/kg TM4, TM6, and TM4-ΔC, respectively. Pretreatment of mice with either inhibitory peptide dramatically decreased systemic IL-6 and TNF-α levels measured 2 h after LPS challenge; after the treatment, the plasma cytokine levels were only 5-15% of cytokine levels induced in the PBS-treated group (FIG. 10A). The effect was lasting; TM4 and TM6 significantly decreased circulating levels of both cytokines at every time point throughout the observation period (FIG. 10B).

Optimization of Peptide Dose

When used at a lower dose of 2.5 nmol/g, TM4 appears to affect the circulating TNF-a equally strongly as it does at 10 nmol/g. However, the lower dose was less efficacious against the circulating IL-6 levels, especially at the later time points. A similar decrease in the TM6 dose resulted in a less efficient inhibition of both cytokines. Interestingly, these results, obtained in in vivo experiments, parallel very closely the effects of low peptide doses on macrophage expression of cytokine mRNA (FIG. 5A, 5B). Increasing the peptide dose to 25 nmol/g did not augment the efficiency of TM4 and TM4-ΔC with respect to circulating IL-6 at 4- or 8-h time points. Based on these observations, the dose of 10 nmol/g was chosen for all subsequent experiments.

Effect of Injection Route

Efficient cellular uptake of cell-permeating peptides is well established for monolayers of cells in culture; however, the tissue permeability of peptides is expected to be lower. Diminished peptide permeability through the tissues of the body might limit their inhibitory efficacy in vivo. Results of experiments shown in FIG. 10B demonstrate that peptides effectively mitigate the TLR4-driven inflammatory symptoms when administered via the same route as the TLR agonist, that is, i.p. To understand whether peptides might be effective as systemic inhibitors of TLR4, we used separate routes of administration for the TLR4 agonist and TLR4 antagonists in the next series of experiments. Peptides (10 nmol/g) were injected i.v.; LPS was administered i.p. Intravenous injection of TM4 or TM4-ΔC significantly lowered the levels of circulating IL-6 and TNF-α throughout the 8-h observation period following the LPS injection (FIG. 10C). However, the inhibitory effect of i.v. injection was less compared with that after i.p. administration of an inhibitory peptide (FIG. 10C, 10B, respectively). Although a statistically significant difference in cytokine levels after i.p. versus i.v. treatment was detected only for the effect of TM4 on IL-6 4 h after LPS injection ($p<0.01$, data not shown), for all other time points, the p values of the difference between the untreated and i.v.-treated group were lower than between the untreated and i.p.-treated animals for both TM4 and TM4-ΔC peptides (FIG. 10B, 10C, and data not shown). These data show that the i.v. injection of decoy peptide is less effective compared with i.p. administration in this model of inflammation; nevertheless, the results indicate that the peptides are efficient systemic TLR inhibitors.

Effects of Timing of Peptide Treatment

TLR activation launches a complex chain of signaling events that ultimately result in production of multiple cytokines. Secreted cytokines act back on cells and activate a multitude of different signaling pathways, many of which help to sustain inflammation. In our previously described experiments, mice were pretreated with inhibitory peptides before activation of TLR signaling by LPS. We next wanted to determine whether the peptides administered after LPS are still effective for mitigation of TLR4-driven inflammatory symptoms. In this series of experiments, mice were first challenged i.p. with LPS (1 µg/g); peptides were injected at the dose of 10 nmol/g i.p. 30 min after LPS. The administration of inhibitory peptides 30 min after LPS did not affect levels of circulating TNF-α and IL-6 measured 1 h after LPS administration (i.e., 30 min after administration of peptides) (FIG. 10E). However, 2 h after LPS challenge, that is, 1.5 h after injection of peptides, the plasma levels of both cytokines were markedly diminished in mice treated with any of the three inhibitory peptides tested, TM4, TM6, or TM-AC (FIG. 10D, 6E). The observed diminution in the cytokine levels at 2, 4, and 8 h after LPS was less than that in the experiments when mice were pretreated with inhibitory peptides (FIG. 10A, 10B, 10D, 10E). TM8/9, a peptide that did not inhibit macrophage signaling in vitro, did not affect the LPS-induced cytokines in vivo 2 h after LPS challenge or thereafter (FIG. 10E). Our data suggest that both prophylactic and therapeutic administration of peptides mitigate the inflammatory response to LPS.

Inhibitory Peptides Protect Mice from a Lethal LPS Challenge

TM4, TM6, and TM4-ΔC strongly suppress systemic cytokine response induced by a sublethal LPS dose. We next studied whether inhibitory peptides protect mice from a lethal LPS challenge. TR6, a previously described inhibitory peptide derived from the third helical region of TRAP (30), was also included in this study as an additional control. C57BL/6J mice were injected i.p. with 17.5 µg/g LPS. This dose induced 100% mortality in the control group (FIG. 10F). Pretreatment of mice with 10 nmol/g TM4 or TM4-ΔC rescued all animals from the lethal LPS dose (FIG. 10F). TM6 also dramatically improves survival compared with the untreated group; however, 3 of 13 animals died after LPS challenge in this group. TR6, an inhibitory TRAP peptide that shares significant sequence similarity with TM6, improved animal survival comparably to TM6 (FIG. 10F). In an additional control series of experiments, we used peptide TM8/9 as this peptide did not inhibit TLR4 in in vitro tests. Although we had one survivor in the group of seven animals injected with 17.5 µg/g LPS following pretreatment with TM8/9, the difference in survival rate was highly significant between each of the control groups and the TM4-, TM6-, or TM4-ΔC-treated group (p, 0.0012, for all pairs). The peptide-treated survivors appeared active and healthy at the time the experiments were terminated, 7 d after injection of LPS.

We next studied whether the TRAM decoy peptides are effective when administered therapeutically, that is, in our model of the disease, after injection of LPS. TM4-ΔC was chosen for these tests. The peptide was administered i.p. 3 h after i.p. injection of LPS. Five of seven animals survived the lethal LPS challenge in this group, whereas no animals survived in the untreated group (0 of 12) and all animals (10 of 10) survived in the group pretreated with TM4-ΔC (FIG. 10G). These data demonstrate that inhibitory peptides have strong potential as therapeutics, because the difference in survival rate between the untreated and the group treated with TM4-ΔC therapeutically is highly significant (p=0.009 as determined by the Gehan-Breslow-Wilcoxon test). The results presented strongly suggest that select decoy peptides effectively lessen the systemic inflammatory response induced by activation of TLR4 and, therefore, might be effective for treatment of septic shock.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Toshchakov, V. Y., H. Szmacinski, L. A. Couture, J. R. Lakowicz, and S. N. Vogel. 2011. Targeting TLR4 signaling by TLR4 Toll/IL-1 receptor domain-derived decoy peptides: identification of the TLR4 Toll/IL-1 receptor domain dimerization interface. *J Immunol* 186:4819-4827.
2. Kawai, T., and S. Akira 2010. The role of pattern-recognition receptors in innate immunity: update on Toll-like receptors. *Nat Immunol* 11:373-384.
3. Knapp, S. 2010. Update on the role of Toll-like receptors during bacterial infections and sepsis. *Wien Med Wochenschr* 160:107-111.
4. Chan, S. L., L. Y. Low, S. Hsu, S. Li, T. Liu, E. Santelli, G. Le Negrate, J. C. Reed, V. L. Woods, Jr., and J. Pascual. 2009. Molecular mimicry in innate immunity: crystal structure of a bacterial TIR domain. *J Biol Chem* 284: 21386-21392.
5. Newman, R. M., P. Salunkhe, A. Godzik, and J. C. Reed. 2006. Identification and characterization of a novel bacterial virulence factor that shares homology with mammalian Toll/interleukin-1 receptor family proteins. *Infect Immun* 74:594-601.
6. Cirl, C., A. Wieser, M. Yadav, S. Duerr, S. Schubert, H. Fischer, D. Stappert, N. Wantia, N. Rodriguez, H. Wagner, C. Svanborg, and T. Miethke. 2008. Subversion of Toll-like receptor signaling by a unique family of bacterial Toll/interleukin-1 receptor domain-containing proteins. *Nat Med* 14:399-406.
7. Botos, I., D. M. Segal, and D. R. Davies. 2011. The structural biology of Toll-like receptors. *Structure* 19:447-459.
8. Rock, F. L., G. Hardiman, J. C. Timans, R. A. Kastelein, and J. F. Bazan. 1998. A family of human receptors structurally related to *Drosophila* Toll. *Proc Natl Acad Sci USA* 95:588-593.
9. Valkov, E., A. Stamp, F. Dimaio, D. Baker, B. Verstak, P. Roversi, S. Kellie, M. J. Sweet, A. Mansell, N. J. Gay, J. L. Martin, and B. Kobe. 2011. Crystal structure of Toll-like receptor adaptor MAL/TIRAP reveals the molecular basis for signal transduction and disease protection. *Proc Natl Acad Sci USA* 108:14879-14884.
10. Monie, T. P., M. C. Moncrieffe, and N. J. Gay. 2009. Structure and regulation of cytoplasmic adapter proteins involved in innate immune signaling. *Immunol Rev* 227: 161-175.
11. Nunez Miguel, R., J. Wong, J. F. Westoll, H. J. Brooks, L. A. O'Neill, N. J. Gay, C. E. Bryant, and T. P. Monie. 2007. A dimer of the Toll-like receptor 4 cytoplasmic domain provides a specific scaffold for the recruitment of signalling adaptor proteins. *PLoS ONE* 2:e788.
12. Jin, M. S., and J. O. Lee. 2008. Structures of the toll-like receptor family and its ligand complexes. *Immunity* 29:182-191.
13. Vogel, S. N., K. A. Fitzgerald, and M. J. Fenton. 2003. TLRs: differential adapter utilization by toll-like receptors mediates TLR-specific patterns of gene expression. *Mol Interv* 3:466-477.
14. Horng, T., G. M. Barton, and R. Medzhitov. 2001. TRAP: an adapter molecule in the Toll signaling pathway. *Nat Immunol* 2:835-841.
15. Fitzgerald, K. A., E. M. Palsson-McDermott, A. G. Bowie, C. A. Jefferies, A. S. Mansell, G. Brady, E. Brint, A. Dunne, P. Gray, M. T. Harte, D. McMurray, D. E. Smith, J. E. Sims, T. A. Bird, and L. A. O'Neill. 2001. Mal (MyD88-adapter-like) is required for Toll-like receptor-4 signal transduction. *Nature* 413:78-83.

16. Kagan, J. C., and R. Medzhitov. 2006. Phosphoinositide-mediated adaptor recruitment controls Toll-like receptor signaling. *Cell* 125:943-955.
17. Homg, T., G. M. Barton, R. A. Flavell, and R. Medzhitov. 2002. The adaptor molecule TRAP provides signalling specificity for Toll-like receptors. *Nature* 420:329-333.
18. Toshchakov, V. Y., and S. N. Vogel. 2007. Cell-penetrating TIR BB loop decoy peptides a novel class of TLR signaling inhibitors and a tool to study topology of TIR-TIR interactions. *Expert Opin Bioi Ther* 7:1035-1050.
19. Toshchakov, V. U., S. Basu, M. J. Fenton, and S. N. Vogel. 2005. Differential involvement of BB loops of toll-IL-1 resistance (TIR) domain-containing adapter proteins in TLR4-versus TLR2-mediated signal transduction. *J Immunol* 175:494-500.
20. Pace, C. N., F. Vajdos, L. Fee, G. Grimsley, and T. Gray. 1995. How to measure and predict the molar absorption coefficient of a protein. *Protein Sci* 4:2411-2423.
21. Derossi, D., A. H. Joliot, G. Chassaing, and A. Prochiantz. 1994. The third helix of the Antennapedia homeodomain translocates through biological membranes. *J Bioi Chem* 269:10444-10450.
22. Toshchakov, V. Y., M. J. Fenton, and S. N. Vogel. 2007. Cutting Edge: Differential inhibition of TLR signaling pathways by cell-permeable peptides representing BB loops of TLRs. *J Immunol* 178:2655-2660.
23. Toshchakov, V., B. W. Jones, P. Y. Perera, K. Thomas, M. J. Cody, S. Zhang, B. R. Williams, J. Major, T. A. Hamilton, M. J. Fenton, and S. N. Vogel. 2002. TLR4, but not TLR2, mediates IFN-beta-induced STAT1alpha/beta-dependent gene expression in macrophages. *Nat Immunol* 3:392-398.
24. Yamamoto, M., S. Sato, H. Hemmi, H. Sanjo, S. Uematsu, T. Kaisho, K. Hoshino, O. Takeuchi, M. Kobayashi, T. Fujita, K. Takeda, and S. Akira 2002. Essential role for TRAP in activation of the signalling cascade shared by TLR2 and TLR4. *Nature* 420:324-329.
25. Kenny, E. F., S. Talbot, M. Gong, D. T. Golenbock, C. E. Bryant, and L. A. O'Neill. 2009. MyD88 adaptor-like is not essential for TLR2 signaling and inhibits signaling by TLR3. *J Immunol* 183:3642-3651.
26. Slack, J. L., K. Schooley, T. P. Bonnert, J. L. Mitcham, E. E. Qwamstrom, J. E. Sims, and S. K. Dower. 2000. Identification of two major sites in the type I interleukin-1 receptor cytoplasmic region responsible for coupling to proinflammatory signaling pathways. *J Biol Chem* 275: 4670-4678.
27. Nyman, T., P. Stenmark, S. Flodin, I. Johansson, M. Hammarstrom, and P. Nordlund. 2008. The crystal structure of the human toll-like receptor 10 cytoplasmic domain reveals a putative signaling dimer. *J Biol Chem* 283:11861-11865.
28. Xu, Y., X. Tao, B. Shen, T. Homg, R. Medzhitov, J. L. Manley, and L. Tong. 2000. Structural basis for signal transduction by the Toll/interleukin-1 receptor domains. *Nature* 408:111-115.
29. Verstak, B., K. Nagpal, S. P. Bottomley, D. T. Golenbock, P. J. Hertzog, and A. Mansell. 2009. MyD88 adapter-like (Mal)/TIRAP interaction with TRAF6 is critical for TLR2- and TLR4-mediated NF-kappaB proinflammatory responses. *J Biol Chem* 284:24192-24203.
30. Couture, L. A., W. Piao, L. W. Ru, S. N. Vogel, and V. Y. Toshchakov. 2012. Targeting Toll-like Receptor (TLR) Signaling by Toll/Interleukin-1 Receptor (TIR) Domain-containing Adapter Protein/MyD88 Adapter-like (TIRAP/Mal)-derived Decoy Peptides. *J Biol Chem* 287:24641-24648.
31. Piao, W., S. N. Vogel, and V. Y. Toshchakov. 2013. Inhibition of TLR4 Signaling by TRAM-derived Decoy Peptides in Vitro and in Vivo. *J Immunol* Accepted.
32. Bartfai, T., M. M. Behrens, S. Gaidarova, J. Pemberton, A. Shivanyuk, and J. Rebek, Jr. 2003. A low molecular weight mimic of the Toll/IL-1 receptor/resistance domain inhibits IL-1 receptor-mediated responses. *Proc Natl Acad Sci USA* 100:7971-7976.
33. Oshiumi, H., M. Sasai, K. Shida, T. Fujita, M. Matsumoto, and T. Seya. 2003. TIR-containing adapter molecule (TI-CAM)-2, a bridging adapter recruiting to Toll-like receptor 4 TICAM-1 that induces interferon-beta. *J. Biol. Chem.* 278:49751-49762.
34. Hirschfeld, M., Y. Ma, J. H. Weis, S. N. Vogel, and J. J. Weis. 2000. Cutting edge: repurification of lipopolysaccharide eliminates signaling through both human and murine Toll-like receptor 2. *J. Immunol.* 165: 618-622.
35. Wu, B., B. Xin, M. Jin, T. Wei, and Z. Bai. 2011. Comparative and phylogenetic analyses of three TIR domain-containing adaptors in metazoans: implications for evolution of TLR signaling pathways. *Dev. Comp. Immunol.* 35: 764-773.
36. Medvedev, A. E., W. Piao, J. Shoenfelt, S. H. Rhee, H. Chen, S. Basu, L. M. Wahl, M. J. Fenton, and S. N. Vogel. 2007. Role of TLR4 tyrosine phosphorylation in signal transduction and endotoxin tolerance. *J. Biol. Chem.* 282: 16042-16053.

What is claimed is:

1. A TIR-derived decoy peptide selected from the group consisting of:

TRAP based, TIR-derived decoy peptides
  TR3 (RQIKIWFQNRRMKWKKEGSQASLRCF; SEQ ID NO:1),
  TR5 (RQIKIWFQNRRMKWKKELCQALSRSHCR; SEQ ID NO:2),
  TR6 (RQIKIWFQNRRMKWKKPGFLRDPWCK-YQML; SEQ ID NO:3),
  TR9 (RQIKIWFQNRRMKWKKAAYPPELR-FMYYVD; SEQ ID NO:4),
  TR11 (RQIKIWFQNRRMKWKKGG-FYQVKEAVIHY; SEQ ID NO:5), TRAM based, TIR-derived decoy peptides
  TM4-ΔC (RQIKIWFQNRRMKWKKIVFAEMPCG; SEQ ID NO:7),
  TM6 (RQIKIWFQNRRMKWKKENFLRDTWCN-FQFY; SEQ ID NO:8), TRIF based, TIR-derived decoy peptides
  TF5 (RQIKIWFQNRRMKWKKCLQDAIDHSGFT; SEQ ID NO:10),
  TF5-ΔC (RQIKIWFQNRRMKWKKCLQDAIDHS; SEQ ID NO:11), MyD88 based, TIR-derived decoy peptides
  M3 (RQIKIWFQNRRMKWKKEQTDYRLKLC; SEQ ID NO:12),
  M5 (RQIKIWFQNRRMKWKKIASELIEKRCRRM; SEQ ID NO:14), TLR2 based, TIR-derived decoy peptides
  2R1 (RQIKIWFQNRRMKWKKRKPKKAPCRDV-CYD; SEQ ID NO:20),
  2R3 (RQIKIWFQNRRMKWKKENSDPPFKLC; SEQ ID NO:21),
  2R9 (RQIKIWFQNRRMKWKKPQRFCKLRKIMNT; SEQ ID NO:22),
  and
  2DD-αD (RQIKIWFQNRRMKWKKEPIERKAIPQR-FCK; SEQ ID NO:24), and variants thereof having one or two amino acid changes, independently selected from additions, substitutions and deletions, in the TIR-domain segment of the peptide.

2. A TIR-derived decoy peptide selected from the group consisting of:

TIRAP based, TIR-derived decoy peptides
  TR3 (RQIKIWFQNRRMKWKKEGSQASLRCF; SEQ ID NO: 1),
  TR5 (RQIKIWFQNRRMKWKKELCQALSRSHCR; SEQ ID NO:2),
  TR6 (RQIKIWFQNRRMKWKKPGFLRDPWCK-YQML; SEQ ID NO:3),
  TR9 (RQIKIWFQNRRMKWKKAAYPPELR-FMYYVD; SEQ ID NO:4),
  TR11 (RQIKIWFQNRRMKWKKGG-FYQVKEAVIHY; SEQ ID NO:5), TRAM based, TIR-derived decoy peptides
  TM4-ΔC (RQIKIWFQNRRMKWKKIVFAEMPCG; SEQ ID NO:7),

TM6 (RQIKIWFQNRRMKWKKENFLRDTWCN-FQFY; SEQ ID NO:8),

TRIF based, TIR-derived decoy peptides

TF5 (RQIKIWFQNRRMKWKKCLQDAIDHSGFT; SEQ ID NO: 10),

TF5-ΔC (RQIKIWFQNRRMKWKKCLQDAIDHS; SEQ ID NO: 11),

MyD88 based, TIR-derived decoy peptides

M3 (RQIKIWFQNRRMKWKKEQTDYRLKLC; SEQ ID NO: 12),

M5 (RQIKIWFQNRRMKWKKIASELIEKRCRRM; SEQ ID NO: 14),

TLR2 based, TIR-derived decoy peptides

2R1 (RQIK1WFQNRRMKWKKRKPKKAPCRDVCYD; SEQ ID NO:20),

2R3 (RQIK1WFQNRRMKWKKENSDPPFKLC; SEQ ID NO:21),

2R9 (RQIK1WFQNRRMKWKKPQRFCKLRKIMNT; SEQ ID NO:22), and

2DD-αD (RQIKIWFQNRRMKWKKEPIERKAIPQR-FCK; SEQ ID NO:24).

* * * * *